(12) United States Patent
Rusch et al.

(10) Patent No.: US 12,303,374 B2
(45) Date of Patent: May 20, 2025

(54) CELL ENCAPSULATION DEVICES WITH CONTROLLED CELL BED THICKNESS

(71) Applicant: W.L. Gore & Associates, Inc., Newark, DE (US)

(72) Inventors: Greg Rusch, Newark, DE (US); Edward H. Cully, Newark, DE (US)

(73) Assignee: W. L. Gore & Associates, Inc., Newark, DE (US)

( * ) Notice: Subject to any disclaimer, the term of this patent is extended or adjusted under 35 U.S.C. 154(b) by 1088 days.

(21) Appl. No.: 17/272,360

(22) PCT Filed: Aug. 30, 2019

(86) PCT No.: PCT/US2019/049007
§ 371 (c)(1),
(2) Date: Mar. 1, 2021

(87) PCT Pub. No.: WO2020/068366
PCT Pub. Date: Apr. 2, 2020

(65) Prior Publication Data
US 2021/0315682 A1 Oct. 14, 2021

Related U.S. Application Data

(60) Provisional application No. 62/736,553, filed on Sep. 26, 2018.

(51) Int. Cl.
*A61F 2/02* (2006.01)
(52) U.S. Cl.
CPC ...... *A61F 2/022* (2013.01); *A61F 2210/0014* (2013.01); *A61F 2220/005* (2013.01);
(Continued)

(58) Field of Classification Search
CPC .. A61F 2/0077; A61F 2002/0091; A61F 2/02; A61F 2210/00; A61F 2250/0067;
(Continued)

(56) References Cited

U.S. PATENT DOCUMENTS 3,953,566 A   4/1976   Gore
5,786,216 A * 7/1998   Dionne .................... B01J 13/02
                                                        435/395
(Continued)

FOREIGN PATENT DOCUMENTS

WO    WO94/13469    6/1994

OTHER PUBLICATIONS

International Preliminary Report on Patentability received for PCT Patent Application No. PCT/US2019/049007, mailed on Apr. 8, 2021, 9 pages.

(Continued)

*Primary Examiner* — Jason E Flick
(74) *Attorney, Agent, or Firm* — Faegre Drinker Biddle & Reath LLP

(57) ABSTRACT

An implantable containment apparatus for receiving and retaining a biological moiety, including a plurality of cells, for insertion into a patient, such as into a tissue bed, is disclosed. The device includes a cell encapsulating pouch that forms and interior volume having a reservoir space for receiving cells, where the reservoir space includes first and second interior surfaces, and a tensioning member to maintain an average distance between the first interior surface and the second interior surface.

32 Claims, 8 Drawing Sheets

(52) U.S. Cl.
CPC .............. *A61F 2220/0058* (2013.01); *A61F 2220/0075* (2013.01); *A61F 2250/0012* (2013.01); *A61F 2250/0023* (2013.01); *A61F 2250/0069* (2013.01)

(58) Field of Classification Search
CPC ........ A61F 2002/0081; A61F 2002/009; A61F 2210/0004; A61F 2210/0014; A61F 2210/0071; A61F 2210/0076; A61F 2240/001; A61F 2250/0068; A61F 2/022; A61F 2220/005; A61F 2220/0058; A61F 2220/0075; A61F 2250/0012; A61F 2250/0023; A61F 2250/0069; A61L 27/00; A61L 29/00; A61L 27/16; A61L 27/36; A61L 27/54; A61L 27/56; A61M 2202/00; A61M 2202/0007; A61M 2202/09; A61M 31/00; A61M 2202/097; A61M 31/002; A61M 5/00; A61M 5/14276; C12N 5/00; C12N 5/0012
See application file for complete search history.

(56) References Cited

U.S. PATENT DOCUMENTS

| | | |
|---|---|---|
| 5,814,405 A | 9/1998 | Branca |
| 8,808,848 B2 | 8/2014 | Bacino |
| 2018/0125632 A1 | 5/2018 | Cully et al. |
| 2018/0126134 A1 | 5/2018 | Cully et al. |
| 2018/0263238 A1* | 9/2018 | Flanagan ............... B29C 65/74 |

OTHER PUBLICATIONS

International Search Report and Written Opinion received for PCT Patent Application No. PCT/US2019/049007, mailed on Dec. 17, 2019, 12 pages.

* cited by examiner

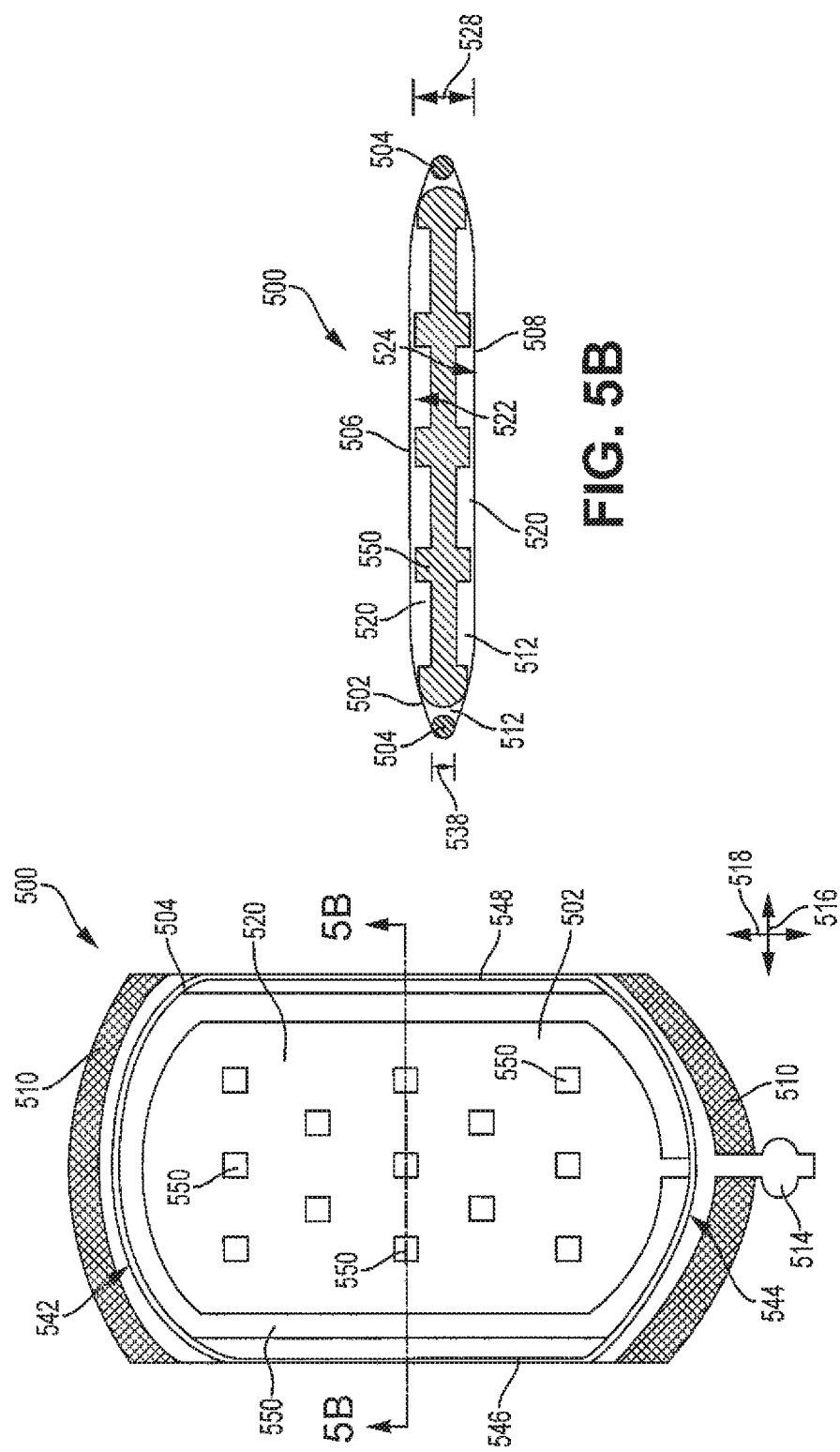

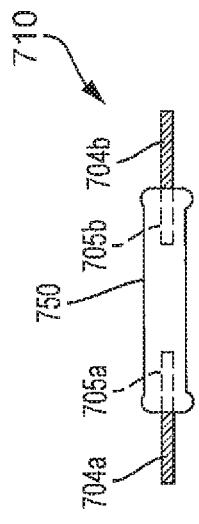
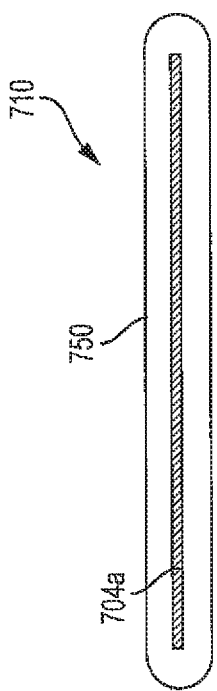
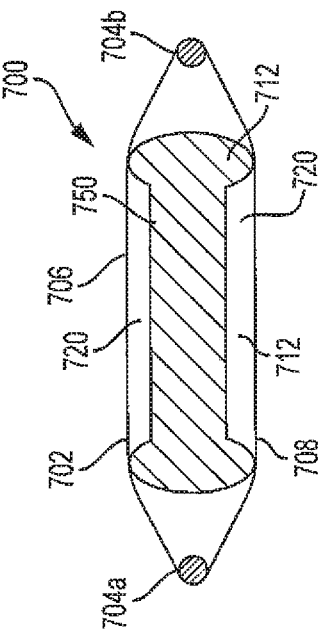
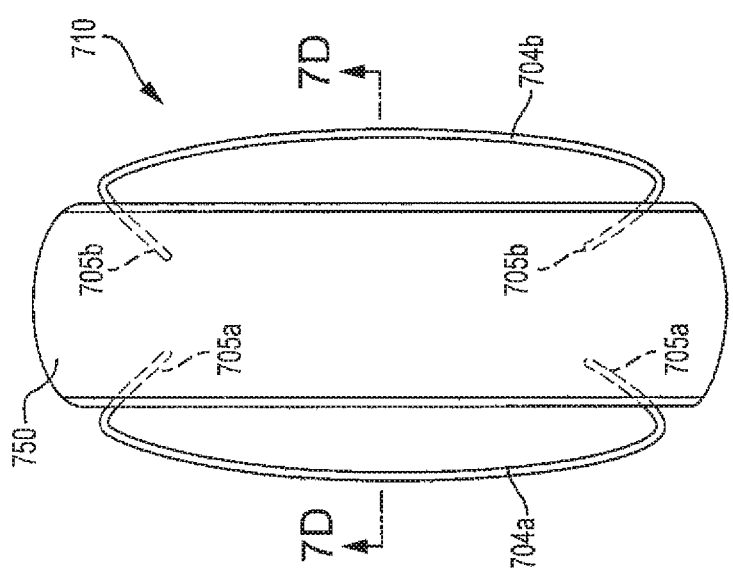
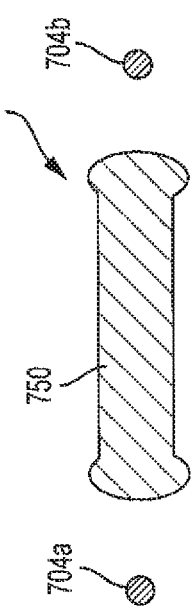

CELL ENCAPSULATION DEVICES WITH CONTROLLED CELL BED THICKNESS

FIELD

The present invention relates to the field of medical devices and implantable medical devices and, in particular, to a device and method for encapsulating and implanting cells into a patient.

BACKGROUND

Biological therapies are increasingly viable methods for treating peripheral artery disease, aneurysm, heart disease, Alzheimer's and Parkinson's diseases, autism, blindness, diabetes, and other pathologies.

With respect to biological therapies in general, cells, viruses, viral vectors, bacteria, proteins, antibodies, and other bioactive moieties may be introduced into a patient by surgical or interventional methods that place the bioactive moiety into a tissue bed of a patient. Often the bioactive moieties are first placed in a device that is then inserted into the patient. Alternatively, the device may be inserted into the patient first with the bioactive moiety added later.

To maintain a viable and producing population of bioactive moieties (e.g., cells), the bioactive moieties must maintain access to nutrients, such as provided by blood flowing through adjacent blood vessels. This access to nutrients requires proximity to the membrane separating the encapsulated cells, i.e., the cell bed, from the tissue bed in which they are implanted. While an implantable device may be designed with such considerations in mind, the device often is subjected to in vivo forces (e.g., compressive forces caused by patient contact with another person or an object) that distort or disrupt the designed and desired structure of the device and the cell bed. Thus, an implantable device containing cells (or other bioactive moieties) not only must be constructed so that nutrients can reach the encapsulated cells, but also must be able to withstand in vivo forces that could distort or disrupt the designed and desired structure of the device and the cell bed. There remains a need for devices that encapsulate cells (or other bioactive moieties) where the devices are structured to control cell bed thickness and/or restore cell bed thickness after a deformation.

SUMMARY

The terms "invention," "the invention," "this invention" and "the present invention," as used in this document, are intended to refer broadly to all of the subject matter of this patent application and the claims below. Statements containing these terms should be understood not to limit the subject matter described herein or to limit the meaning or scope of the patent claims below. Covered embodiments of the invention are defined by the claims, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification, any or all drawings, and each claim.

The present disclosure provides devices and methods for encapsulating cells for insertion into a patient as biological therapy. The devices include a cell encapsulating pouch formed from a membrane or membrane composite that surrounds the cells and through which the cells can receive nutrients from and provide biological therapy to a host body. The devices further include a tensioning member or members that maintain the designed structure of the cell encapsulating pouch and cell bed.

In some embodiments, a cell encapsulation device described herein includes a cell encapsulating pouch including a first layer sealed along a portion of its periphery to a second layer along a portion of its periphery to define an interior volume between the first and second layers, where the interior volume includes a first interior surface and an opposing second interior surface spaced apart from the first interior surface. The interior volume includes the entire volume inside the cell encapsulating pouch whether empty or occupied by a structural element. At least one tensioning member can be disposed within the interior volume and can contact at least two opposing portions of its periphery to maintain an average distance between the first interior surface and the second interior surface. The cell encapsulating device further includes a reservoir space for receiving cells within the interior volume between the first and second interior surfaces and inward from the tensioning member(s). The reservoir space is only the portion of the interior volume that is available for receiving cells and does not include volume occupied by structural elements. Optionally, the cell encapsulation device may further include at least one port in fluid communication with the reservoir space.

In some embodiments, the first and second layers of a cell encapsulating pouch comprise top and bottom portions of a single tube-shaped membrane or membrane composite that is at least partially flattened, and where the first layer is sealed to the second layer at least at one end of the tube-shaped membrane or membrane composite. In other embodiments, the first and second layers of a cell encapsulating pouch comprise two separate membranes or membrane composites.

In some embodiments, a cell encapsulation device described herein may comprise at least one cell displacing core within the interior volume. In other embodiments, a cell encapsulating device described herein may comprise a plurality of structural spacers within the interior volume.

The tensioning member of a cell encapsulation device described herein may be in fluid communication with the reservoir space or alternatively may be isolated from the reservoir space. For example, the first layer may be sealed to the second layer between the tensioning member and the reservoir space to isolate the tensioning member from the reservoir space. The seal may comprise a thickness that defines the average thickness between the first interior surface and the second interior surface.

In some embodiments of a cell encapsulation device described herein, the tensioning member exerts opposing lateral forces away from the reservoir space. Optionally, the tensioning member(s) may be a shape memory elastomer or a shape memory polymer. Optionally, the tensioning member may be a frame including opposing ends that are non-linear and opposing sides that are linear to provide uniform tension across a length of the cell encapsulating pouch. The tensioning member(s) may adjustable between a deformed configuration and an undeformed configuration such that a distance between at least two opposing sides of the tensioning member(s) is adjustable. For example, the distance between the at least two opposing sides in the deformed configuration may be less than the distance between the at least two opposing sides in the undeformed configuration.

In some embodiments of a cell encapsulation device described herein, the average distance between the first interior surface and the second interior surface is at least a thickness of the tensioning member(s). In other embodiments, the average distance between the first interior surface and the second interior surface is less than a thickness of the tensioning member(s).

Optionally, a cell encapsulating pouch described herein may comprise a vascularizing layer. Optionally, the cell encapsulating pouch is a multilayered membrane or membrane composite including an outer vascularizing layer and an inner cell retentive layer adjacent to the outer vascularizing layer.

In some embodiments, a cell encapsulation device described herein comprises a plurality of interconnected containment tubes, where each of the containment tubes comprises a first end, a second end opposite the first end, and interior volume or reservoir space located within each containment tube for retaining the cells. The containment tubes may optionally be interconnected by welds, quilting, adhesive, or structural supports. The device may further comprise a tensioning member disposed around at least a portion of a perimeter of the plurality of containment tubes, where the tensioning member maintains an average thickness of each of the containment tubes. Optionally, the tensioning member may comprise at least two arcuate portions including alternating concavities positioned at the first end and/or at the second end of each of the containment tubes. At least a portion of the tensioning member may be attached to one or more containment tubes with an adhesive. Additionally or alternatively, a portion of the tensioning member may be retained within each of the two outermost containment tubes at opposing ends of the cell encapsulation device.

In some embodiments, a method of encapsulating cells includes providing a cell encapsulation device as described herein where the tensioning member is in a first deformed configuration that provides tension across the cell encapsulating pouch; deforming the tensioning member from the first deformed configuration to a second deformed configuration that is more deformed than the first deformed configuration, whereby the tension on the cell encapsulating pouch is lessened; inserting cells into the reservoir space; and releasing the tensioning member to the first deformed configuration.

In some embodiments, a method of inserting a cell encapsulation device into a patient includes providing a cell encapsulation device as described herein, where the cell encapsulation device further comprises cells disposed in the reservoir space, and where the tensioning member is in a first deformed configuration that provides tension across the cell encapsulating pouch; deforming the tensioning member from the first deformed configuration to a second deformed configuration that is more deformed than the first deformed configuration, whereby the tension on the cell encapsulating pouch is lessened; implanting the cell encapsulation device into a tissue bed of a patient; and releasing the tensioning member to the first deformed configuration.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

FIG. 5A is a schematic of a top view of a cell encapsulation device according to embodiments described herein.

FIG. 5B is a schematic of a cross-section of the cell encapsulation device of FIG. 5A taken along the line 5B-5B in FIG. 5A.

FIGS. 7A-7D are schematics of an embodiment of an insert for a cell encapsulation device.

FIG. 7E is a cross-sectional view of the cell encapsulation device formed when the insert of 7A-7D is placed inside a cell encapsulating pouch.

DETAILED DESCRIPTION

Figures 1A, 1C:
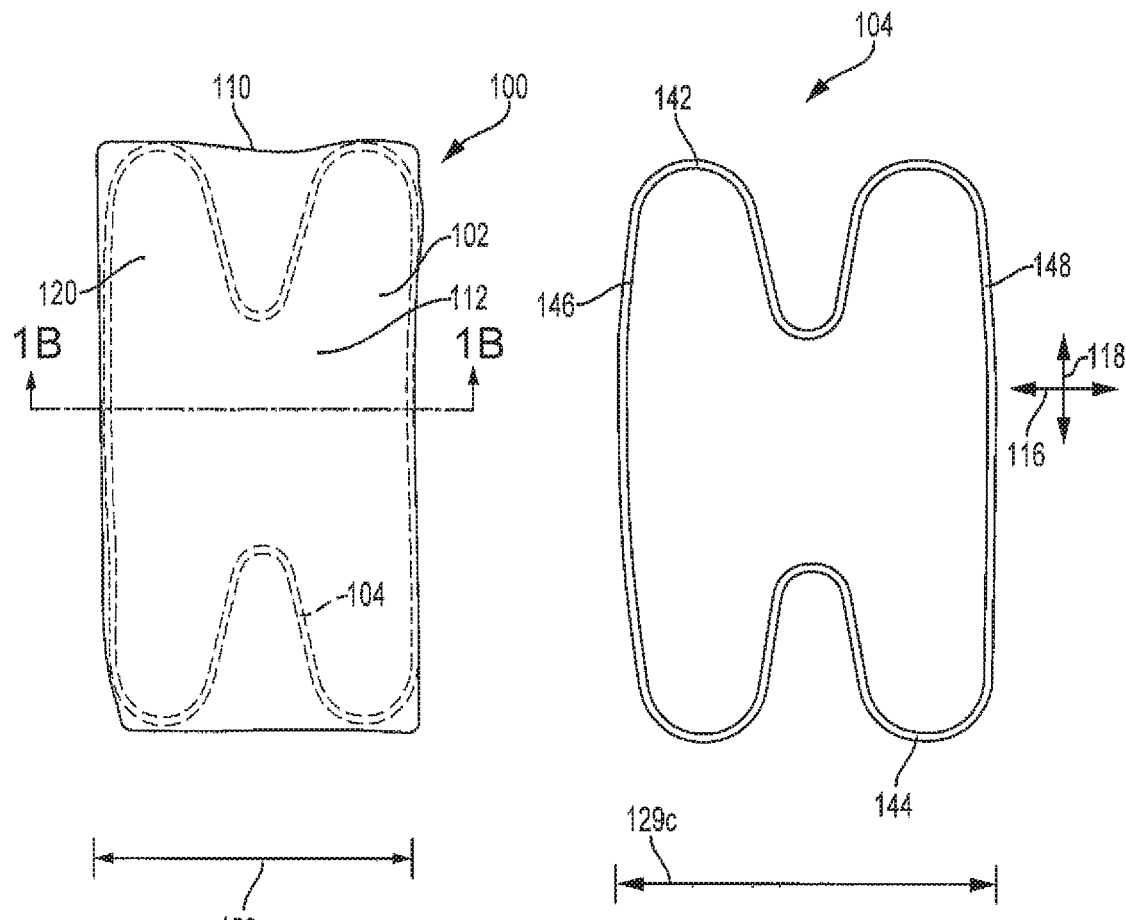
FIG. 1A is a top view of a cell encapsulation device according to embodiments described herein.
FIG. 1C is a top view of the tensioning member of the cell encapsulation device of FIG. 1A.

Persons skilled in the art will readily appreciate that various aspects of the present disclosure can be realized by any number of methods and apparatus configured to perform the intended functions. It should also be noted that the accompanying figures referred to herein are not necessarily drawn to scale, and may be exaggerated to illustrate various aspects of the present disclosure, and in that regard, the figures should not be construed as limiting. Directional references such as "up," "down," "top," "left," "right," "front," and "back," among others are intended to refer to the orientation as illustrated and described in the figure (or figures) to which the components and directions are referencing.

Described herein are therapeutic devices for encapsulating biological moieties, where the biological moieties are implanted into a patient, such as into a tissue bed, to provide biological therapy. The therapeutic devices may include a cell encapsulation device, a drug delivery device, or a gene therapy device. Also described herein are methods for forming the devices, for introducing the biological moieties into the devices, and for introducing the devices into a patient in need of biological therapy. In some embodiments, the device is a tensioned cell encapsulating pouch formed from a membrane or membrane composite, where the cell encapsulating pouch has two spaced apart layers that form a reservoir space for receiving and retaining the biological moiety. A membrane composite includes a membrane and another bio-compatible material, such as a biowoven or nonwoven.

Biological moieties suitable for encapsulation and implantation using the devices described herein include cells, viruses, viral vectors, gene therapies, bacteria, proteins, polysaccharides, antibodies, and other bioactive moieties. For simplicity, herein the biological moiety is referred to as a cell, but nothing in this description limits the biological moiety to cells or to any particular type of cell, and the following description applies also to biological moieties that are not cells. Various types of prokaryotic cells, eukaryotic cells, mammalian cells, non-mammalian cells, and/or stem cells may be used with the cell encapsulation devices of the present invention. In some embodiments, the cells are microencapsulated within a biomaterial of natural or synthetic origin, including, but not limited to, a hydrogel biomaterial.

In some embodiments, the cells secrete a therapeutically useful substance. Such substances include hormones, growth factors, trophic factors, neurotransmitters, lymphokines, antibodies, or other cell products which provide a therapeutic benefit to the device recipient. Examples of such therapeutically useful substances include, but are not limited to, insulin, trophic factors, neurotransmitters, lymphokines, antibodies, growth factors, interleukins, parathyroid hormone, erythropoietin, transferrin, Factor VIII, or other cell products which provide a therapeutic benefit to the device recipient. Non-limiting examples of therapeutic cell products include insulin, growth factors, interleukins, parathyroid hormone, erythropoietin, transferrin, and Factor VIII. Non-limiting examples of suitable growth factors include vascular endothelial growth factor, platelet-derived growth factor, platelet-activating factor, transforming growth factors, bone morphogenetic protein, activin, inhibin, fibroblast growth factors, granulocyte-colony stimulating factor, granulocyte-macrophage colony stimulating factor, glial cell line-derived neurotrophic factor, growth differentiation factor-9, epidermal growth factor, and combinations thereof. It is to be appreciated that throughout this disclosure the terms "cell" or "cells'" could be replaced by "biological moiety" or "biological moieties", respectively. It is to be appreciated that the term "tensioning member" is meant to include one or more tensioning member.

Generally, cell encapsulation devices described herein include a cell encapsulating pouch and tensioning member(s). The cell encapsulating pouch may be formed from a membrane or a membrane composite. The cell encapsulating pouch forms an internal volume that includes at least one reservoir space for receiving cells. In some embodiments, the internal volume includes a plurality of reservoir spaces for receiving cells. The cell encapsulating pouch may include top and bottom layers that can be formed from two separate membranes or membrane composites, one membrane or membrane composite folded to form a top and a bottom layer, or a single tube-shaped membrane or membrane composite that is flattened to form a top and a bottom layer. In any of these embodiments, the top and bottom layers are sealed along at least a portion of their peripheries and the cell encapsulating device has at least one internal volume positioned between the top and bottom layers. In various embodiments, at least a portion of the tensioning member is disposed within the internal volume, the tensioning member exerts an outward force on the cell encapsulating pouch and thereby imparts tension to the top and bottom layers, and where the first layer is sealed to the second layer at least at one end of the tube-shaped membrane or membrane composite. In other embodiments, the first and second layers of a cell encapsulating pouch include two separate membranes or membrane composites.

In various embodiments, a port extends through the cell encapsulating pouch (e.g., through a sealed periphery of the pouch) and is in fluid communication with the reservoir space for inserting cells into the reservoir space. In some embodiments, a cell encapsulating device described herein further includes one or more other structural component, such as seals, spacers (e.g., weld spacers or structural spacers), or a cell displacing core. Generally, a seal is a region where two materials, e.g., the top and bottom layers of the cell encapsulating pouch, are joined without substantially increasing the thickness of the combined materials. A spacer, such as a weld spacer, may also join two materials, but additionally contributes to controlling or maintaining an average distance between the top and bottom layers and may increase the thickness of the combined materials. In various embodiments, seals can be useful to define and/or isolate the reservoir space; spacers can be useful to define a thickness of the reservoir space; and a cell displacing core can be useful to displace cells from the center of the device toward the cell encapsulating pouch to improve transfer of nutrients and waste between the cells and the environment outside the device.

In the cell encapsulation devices described herein, the top and bottom layers are spaced apart from each other by the tensioning member or by an optional spacer or an optional cell displacing core, and a reservoir space for receiving cells lies within the interior volume between interior surfaces of the top and bottom layers. The reservoir space is a portion of the interior volume not occupied by the tensioning member, a spacer (e.g., weld spacer or structural spacer), a cell displacing core, or any other structural component. The reservoir space has a thickness that is the distance between the interior surfaces of the top and bottom layers. The distance between the interior surfaces of the top and bottom layers can be defined by the thickness of the tensioning member or by the thickness of another structural component.

In some embodiments, the top and bottom layers of the cell encapsulating pouch are flexible, but the tensioning member(s) alone or in combination with other structural components maintains the cell encapsulation device as a generally planar structure. In certain embodiments, the tensioning member(s) exerts a force on the cell encapsulating pouch that stretches the cell encapsulating pouch taut in an X-Y plane while the reservoir space thickness is in the Z-dimension. Thus, even when the thickness of the reservoir space is defined by a component other than the tensioning member, the tensioning member maintains the thickness by imparting tension to the cell encapsulating pouch that prevents deformation of the cell encapsulating pouch (such as collapsing or ballooning) and/or restores the defined spacing after deformation. Such deformation may sometimes occur during cell loading, placement of the cell encapsulation device within a target location, cell growth, or various other uses of the cell encapsulation device.

The tensioning member(s) is provided to exert opposing tensioning forces on the cell encapsulating pouch in a direction away from the reservoir space and thereby maintain a reservoir space thickness. A tensioning member may impart tension to a cell encapsulating pouch as a consequence of the tensioning member being in an elastically deformed or compressed configuration when inside the cell encapsulating pouch. The tendency of the tensioning member to return to its undeformed configuration exerts opposing forces on the cell encapsulating pouch and imparts tension to the top and bottom layers. Because the tensioning member imparts tension to the pouch, the materials from which the pouch is made must have a strength necessary to withstand being in a constant state of tension. The tensioning member may be elastically deformable due to being constructed from an inherently elastically deformable material, such as an elastomer. In addition, since the tensioning member can deform the pouch into different configurations, it is necessary that the pouch material is flexible and compliant enough to move and deform along with the tensioning member without causing damage or stress (e.g., permanent folds, wrinkles, creases, holes/breaches etc.).

One non-limiting example of such a tensioning member is an elastomeric o-ring. Examples of useful elastomers are described herein. The shape of the tensioning member or a portion thereof may contribute to the tensioning member being elastically deformable. For example, a frame may be deformable if it has a ring-shape (e.g. circular or oval) or if it is in the shape of a simple polygon having two internal angles that are less than ninety degrees (e.g., a parallelogram that is not a rectangle, a trapezoid shape, a hexagon shape). As another example, a frame including one or more non-linear segments, such as a bowed, helical, or serpentine shaped segment, may be elastically deformable.

In various embodiments, a tensioning member is deformable in at least two opposing lateral directions, such that a distance between opposing sides of the tensioning member is adjustable. Thus, the tensioning member can be deformed by a technician to a narrower configuration (shorter distance between opposing sides) for insertion into the cell encapsulating pouch, and can expand as permitted by the cell encapsulating pouch to a wider but still deformed configuration (longer distance between opposing sides) when released by the technician. In addition to being adjustable during the assembly of a cell encapsulation device, the tensioning member is adjustable during loading and subsequent use of the device. For example, in some cases, the distance between opposing sides of a tensioning member may increase or decrease temporarily during cell loading or during placement of the cell encapsulation device within a patient. Optionally, decreasing (or increasing) the distance may temporarily increase or decrease the thickness of the reservoir space (e.g., to facilitate loading of the cells, etc.), but the tendency of the tensioning member to return to its undeformed configuration and the related forces exerted by the tensioning member on the cell encapsulating pouch return the thickness of the reservoir space to the thickness defined by the structural components.

In some embodiments, the tensioning member(s) is between the first layer and the second layer but isolated from (i.e., not in fluid communication with) the reservoir space. In such an embodiment, the tensioning member will not contact encapsulated cells. Such an embodiment may be useful if the tensioning member is a material that is incompatible with the encapsulated cells, such as, for example, various elastomers. In some embodiments, structural elements may be added within the internal volume of a device to provide a lumen thickness that is different from (lesser or greater than) the tensioning member thickness, and those structural elements may isolate the tensioning member from the reservoir space. In other embodiments, the tensioning member(s) is in fluid communication with the reservoir space. In such embodiments, the tensioning member will contact encapsulated cells and must be a material that is compatible with those cells (e.g., Nitinol). In various embodiments, the material used for the tensioning member(s) may be selected based on whether the tensioning member(s) is in fluid communication with or isolated from the reservoir space, and thus whether the tensioning member may contact encapsulated cells.

In some embodiments, the cell encapsulating pouch is a porous material and may be a composite layer having two or more pore sizes and/or two or more porosities. For example, the cell encapsulating pouch may have a sufficient pore size and/or porosity to allow cell nutrients, beneficial cell products, and cell waste to be exchanged between encapsulated cells and an external environment through the cell encapsulating pouch. As another example, in various embodiments, the pore size of the cell encapsulating pouch may either permit or restrict vascular ingrowth. Such materials are discussed in more detail herein; however, in any cell encapsulation device disclosed herein the first and second layers of the cell encapsulating pouch independently may be a single porous material or a multilayer layer porous material, with each layer having a pore size and/or a porosity that may differ from the pore size and/or the porosity of another layer.

Figure 1B:
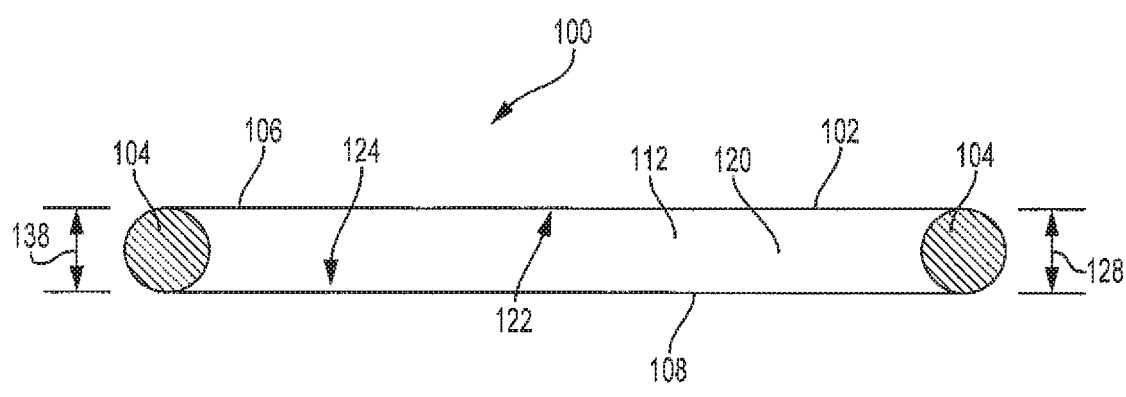
FIG. 1B is a schematic of a cross-section of the cell encapsulation device of FIG. 1A taken along line 1B-1B in FIG. 1A.

FIGS. 1A-B illustrate an embodiment of a cell encapsulation device 100. As illustrated in FIGS. 1A-B, the cell encapsulation device 100 includes a cell encapsulating pouch 102 and tensioning member 104. FIG. 1A is a top view of the cell encapsulation device 100 showing a single tensioning member 104 inside the cell encapsulating pouch 102. FIG. 1B is a cross-section of FIG. 1A across line 1B-1B. FIG. 1C is a top view of the tensioning member 104 before it is inserted into cell encapsulating pouch 102.

The cell encapsulation device 100 includes cell encapsulating pouch 102 as a single membrane formed in a tubular shape that is flattened to form a first layer 106 and a second layer 108. The first and second layers 106, 108 are sealed at their peripheries 110 at one or both ends of the flattened tube. The first layer 106 includes a first interior surface 122 and the second layer 108 includes a second interior surface 124 facing the first interior surface 122 and spaced apart from the first interior surface 122 to define an interior volume 112. The tensioning member 104 is disposed within the interior volume 112, contacts at least two opposing portions of the cell encapsulating pouch 102, and exerts tension on the first and second layers 106, 108. FIGS. 1A-B do not illustrate any optional components, but optionally other components, including weld spacers, other seals, structural spacers, a cell displacing core, or another structural element may be disposed within the interior volume. A port (not shown) can extend through the cell encapsulating pouch (for example, through the sealed periphery 110) and can be in fluid communication with a reservoir space 120.

In the embodiment shown in FIGS. 1A-B, the reservoir space 120 lies between the first and second interior surfaces 122, 124 and inward from the tensioning member 104. The reservoir space 120 has a thickness 128 that is a distance from the first interior surface 122 to the second interior surface 124 and is defined by the tensioning member thickness 138. In this embodiment, tension on the cell encapsulating pouch 102 provided by the tensioning member 104 impedes the collapsing or ballooning of the reservoir space 120 and thus maintains the thickness defined by the tensioning member 104.

In the embodiment illustrated in FIGS. 1A-B, the tensioning member 104 surrounds the reservoir space 120, but in other embodiments it may only partially surround or encompass the reservoir space 120.

As shown in FIG. 1B, the tensioning member 104 may be in fluid communication with the reservoir space 120. Because the tensioning member 104 is in fluid communication with the reservoir space 120 it must be made of a material compatible with any cells to be inserted into the device. Biocompatible materials suitable for tensioning members are described herein.

In some embodiments, the tensioning member(s) of the cell encapsulation device is an insert frame. In the embodiment illustrated in FIGS. 1A-C, the tensioning member 104 is an insert frame that includes opposing ends 142, 144 that are non-linear and opposing sides 146, 148 that are substantially linear. It is to be appreciated that in some embodiments, the sides 146, 148 may be curvilinear or any shape that provides uniform tension across a length of the cell encapsulating pouch 102 (where length is from one opposing end to the other). According to various embodiments, the non-linear ends 142, 144 may be non-linear in the plane defined by the X-axis 116 and Y-axis 118, as shown in FIG. 1C, and/or may be non-linear in the plane defined by the X-axis 116 and the Z-axis (not shown), in an intermediate plane, or in multiple planes. According to various embodiments, the non-linear ends may include one or more s-shapes, as shown in FIG. 1C, or may include other non-linear shapes, such as a curve or helix. Alternatively, frames with other shapes described herein may be utilized as the tensioning member 104.

As illustrated in FIGS. 1A-C, the tensioning member 104 is in an undeformed configuration when separate from the cell encapsulating pouch 102 (FIG. 1C) and is in a deformed/compressed configuration when inside the cell encapsulating pouch 102 (FIGS. 1A-B). Thus, the distance 129a, 129c between opposing sides 146, 148 of the tensioning member 104 is adjustable and the distance 129a in a deformed configuration is less than the distance 129c in the undeformed configuration. The tendency of the tensioning member 104 to return to its undeformed configuration exerts opposing lateral forces on the cell encapsulating pouch 102 and imparts tension to the top and bottom layers 106, 108.

Figure 2:
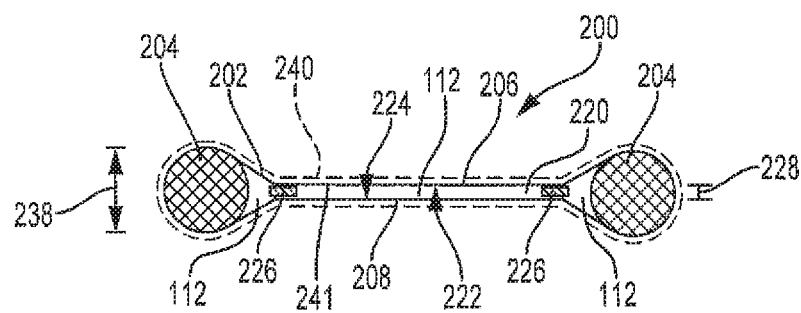
FIG. 2 is a schematic of a cross-section of a cell encapsulation device according to embodiments described herein.

In some embodiments, a cell encapsulating device described herein further includes one or more other components, such as one or more seals, one or more spacers (e.g., weld spacers or structural spacers), or a cell displacing core. FIG. 2 illustrates a cross-sectional view of an embodiment of a cell encapsulation device 200 that is similar in shape to the cell encapsulation device 100, but further includes weld spacers 226 bonding the first and second layers 206, 208 of the cell encapsulating pouch 202. The weld spacers 226 are positioned between the tensioning member 204 and the reservoir space 220. While the tensioning member 204 may have a shape similar to the tensioning member illustrated in FIGS. 1A-C, it need not necessarily have the same shape, and may have an entirely different shape (for example, a circle or an oval).

In the embodiment shown in FIG. 2, the reservoir space 220 lies between the first and second interior surfaces 222, 224 and inward from the weld spacers 226. The reservoir space thickness 228 is a distance from the first interior surface 222 to the second interior surface 224, is defined by the thickness of the weld spacers 226, and is independent of the tensioning member thickness 238 because the weld spacers 226 pinch the top and bottom layers together inward from the tensioning member 204. Thus, in the embodiment illustrated in FIG. 2, the reservoir space thickness 228 is less than the tensioning member thickness 238. As illustrated in FIG. 2, in some embodiments, a cell encapsulating pouch 202 may be a composite material 240, 241 having an outer porous layer 240 and an inner porous layer 241. In some embodiments, the inner porous layer 241 has a small enough pore size to retain the encapsulated cells and restrict ingrowth of tissue. In some embodiments, the outer porous layer 240 allows for ingrowth of tissue to anchor the cell encapsulation device 200 when implanted. The composite material 240, 241 shown in FIG. 2 is optional for any cell encapsulating device described herein, and thus cell encapsulating devices otherwise consistent with FIG. 2 may include a different material as the cell encapsulating pouch. Moreover, embodiments shown in other figures may include the composite material 240, 241 shown in FIG. 2.

The cell encapsulation devices shown in FIGS. 1A-B and FIG. 2 are formed from flattened tube-shaped membranes, but alternatively could be formed from one membrane folded to form a top and a bottom layer, from separate membranes layered to form a top and a bottom layer, or from one or more membrane composites.

Figure 3A:
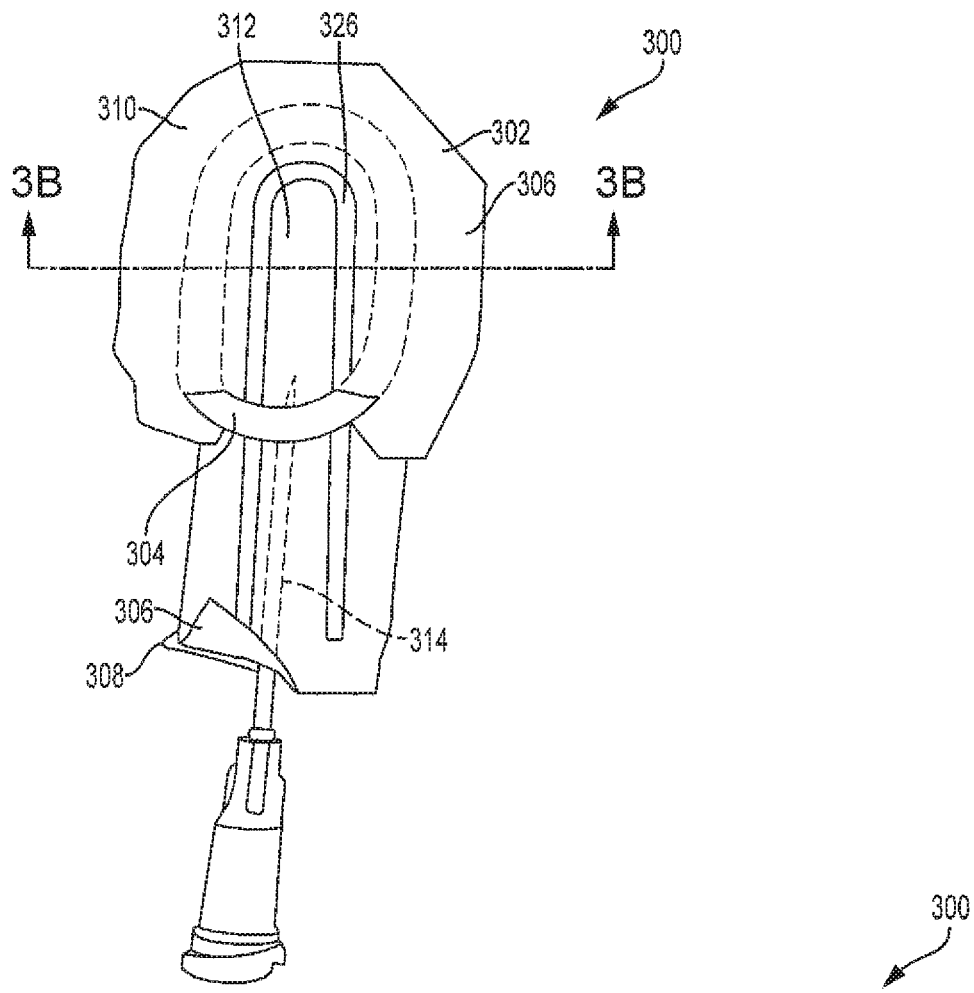
FIG. 3A is a top view of a cell encapsulation device according to embodiments described herein.
Figure 3B:
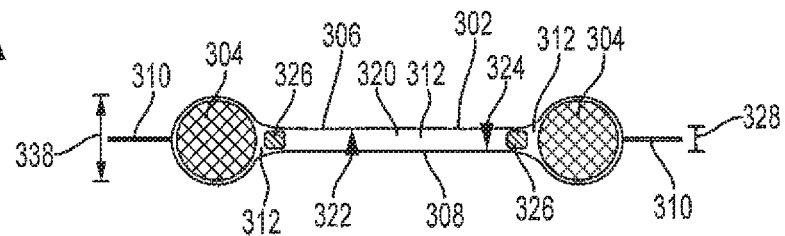
FIG. 3B is a schematic of a cross section of the cell encapsulation device of FIG. 3A taken along line 3B-3B in FIG. 3A.

FIGS. 3A-B illustrate an embodiment of a cell encapsulation device 300 that includes a cell encapsulating pouch 302 and tensioning member 304. FIG. 3A is a top view of the cell encapsulation device 300 showing a single ring-shaped tensioning member 304 inside the cell encapsulating pouch 302. FIG. 3B is a cross-section of FIG. 3A across line 3B-3B.

In the embodiment shown in FIGS. 3A-B, the cell encapsulating pouch 302 includes a first layer 306 and a second layer 308 that are two separate membranes that are sealed along their peripheries 310. Inward from the sealed peripheries 310, the first layer 306 includes a first interior surface 322 and the second layer 308 includes a second interior surface 324 facing the first interior surface 322 and spaced apart from the first interior surface 322 to define an interior volume 312. The tensioning member 304 is disposed within the interior volume, contacts at least two opposing portions of the cell encapsulating pouch 302, and exerts tension on the first and second layers 306, 308. FIG. 3B shows weld spacers 326 disposed within the interior volume inward from the tensioning member 304, but spacers other than weld spacers may alternatively be used. FIG. 3A further illustrates a port 314 that extends through the sealed periphery 310 and is in fluid communication with the reservoir space 320. Optionally a cell displacing core or other structural element may be disposed within the interior volume.

In the embodiment shown in FIGS. 3A-B the reservoir space 320 lies between the first and second interior surfaces 322, 324 and inward from the weld spacers 326. In this embodiment, the reservoir space thickness 328 is a distance from the first interior surface 322 to the second interior surface 324, is defined by the thickness of the weld spacers 326, and is independent from the tensioning member thickness 338 because the weld spacers 326 pinch the top and bottom layers together inward from the tensioning member 304, and the reservoir space thickness 328 is the thickness of the weld spacers 326. Thus, in the embodiment illustrated in FIGS. 3A-B, the reservoir space thickness 328 is less than the tensioning member thickness 338. Alternatively, however, the weld spacers could have a thickness equal to or greater than the tensioning member thickness, and in those embodiments the reservoir space thickness 328 would be equal to or greater than the tensioning member thickness 338. Whatever the reservoir space thickness 328, tension on the cell encapsulating pouch 302 provided by the tensioning member 304 impedes collapsing or ballooning of the reservoir space 320 and thus maintains the thickness defined by the weld spacers 326.

In the embodiment illustrated in FIGS. 3A-B, the tensioning member 304 completely surrounds the reservoir space 320. In other embodiments, the tensioning member may only partially surround or encompass the reservoir space 320. In the embodiment illustrated in FIGS. 3A-B, the weld spacers 326 isolate the tensioning member 304 from the reservoir space 320. Thus, the tensioning member need not be compatible with the cells to be encapsulated.

In the embodiment illustrated in FIGS. 3A-B, the tensioning member 304 is a rubber O-ring. In other examples consistent with this embodiment, the tensioning member could be a different shape or a different material. Inherent flexibility of the tensioning member 304 allows deformation of the tensioning member 304 from a substantially circular configuration to a more ovalar shaped configuration when opposing radially inward forces are applied to the tensioning member 304. The tensioning member 304 is in a deformed configuration when inside the cell encapsulation membrane 302. The tendency of the tensioning member 304 to return to its undeformed configuration exerts opposing lateral forces on the cell encapsulating pouch 302 and imparts tension to the top and bottom layers 306, 308. FIG. 3A further illustrates a port 314 in fluid communication with the reservoir space 320.

Figure 4:
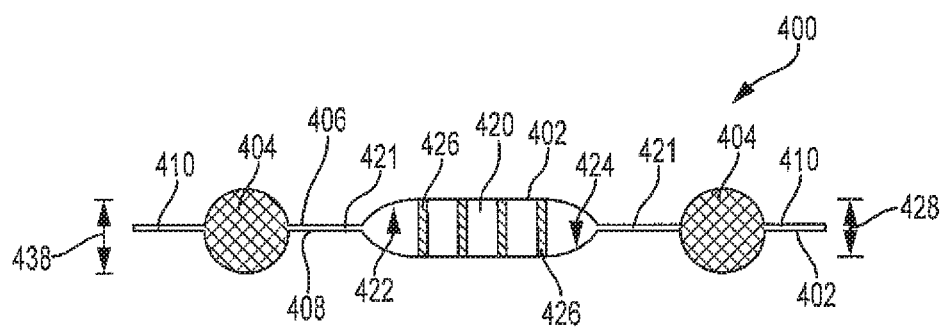
FIG. 4 is a schematic of a cross-section of a cell encapsulation device according to embodiments described herein.

FIG. 4 illustrates a cross-sectional view of another cell encapsulation device 400 that is similar to the cell encapsulation device 300 in that the cell encapsulating pouch 402 is formed from two separate membranes, a first layer 406 and a second layer 408, that are sealed along at least a portion of their peripheries 410. Tensioning member 404 is disposed between the first and second layers 406, 408, contacts at least two opposing portions of the cell encapsulating pouch 402, and exerts tension on the first and second layers 406, 408. Instead of weld spacers, the cell encapsulation device 400 includes a seal 421 that bonds the first and second layers 406, 408 to each other inward from tensioning member 404. Inward from the seal 421, structural spacers 426 separate the first and second layers 406, 408, forming a reservoir space 420 in the portion of the interior volume not occupied by the tensioning member 404 or structural spacers 426.

In this embodiment, the reservoir space thickness 428 is a distance from the first interior surface 422 to the second interior surface 424, is defined by the thickness of the structural spacers 426, and is independent from the tensioning member thickness 438 because the seal 410 binds the first and second layers 406, 408 together inward from the tensioning member 404 and the reservoir space thickness 428 is the thickness of the structural spacers 426 that separate the first and second layers 406. While FIG. 4 illustrates structural spacers 426 having a height less than the tensioning member thickness 438, in some embodiments, the structural spacers 426 could have a thickness equal to or greater than the tensioning member thickness 438, and in those embodiments the reservoir space thickness 428 also would be equal to or greater than the tensioning member thickness 438. Whatever the reservoir space thickness 428, tension on the cell encapsulating pouch 402 provided by the tensioning member 404 impedes collapsing or ballooning of the reservoir space 420 and thus maintains the thickness defined by the weld spacers 426.

As illustrated in FIG. 4, the tensioning member 404 is isolated from the reservoir space 420 by seal 421. In various embodiments, seal 421 may be continuous or discontinuous. When seal 421 is continuous, it isolates the tensioning member 404 from the reservoir spaces 420, and the tensioning member may be made of any suitable material whether or not it is compatible with the encapsulated cells. Where seal 421 is discontinuous (not illustrated), the tensioning member 404 may be in fluid communication with the reservoir space 420 and would then need to be made of a material compatible with the encapsulated cells.

FIGS. 5A-B illustrate an embodiment of a cell encapsulation device 500 that includes a cell displacing core 550. FIG. 5A is a top view of the cell encapsulation device 500, and FIG. 5B is a cross-sectional view of the cell encapsulation device 500 across line 5B-5B. FIGS. 5A-B show the cell encapsulating pouch 502 formed from a single tubular membrane that is flattened to form a first layer 506 and a second layer 508. The tube is sealed at a distal end and/or at a proximal end, both referred to as peripheries 510 of the flattened tube. In alternative embodiments, however, the cell encapsulating pouch 502 could be formed from two separate membranes that are layered and sealed along at least a portion of their peripheries. Alternatively, the cell encapsulating pouch 502 could be formed from one or more membrane composites.

In the embodiments shown in FIGS. 5A-B, the cell encapsulating pouch 502 includes a first layer 506 and a second layer 508 that are sealed along their peripheries 510. The tensioning member 504 is disposed within the reservoir space 520, contacts at least two opposing portions of the cell encapsulating pouch 502, and exerts tension on the first and second layers 506, 508. FIG. 5B shows a cell displacing core 550 disposed within the interior volume inward from the tensioning member 504. FIG. 5A further illustrates a port 514 extending through the sealed periphery 510 and in fluid communication with the reservoir space 520.

In this embodiment, the reservoir space thickness 528 is the distance from the first inner surface 522 to the second interior surface 524, is defined by the thickness of the cell displacing core 550, and is independent from the tensioning member thickness 538 because the cell displacing core 550 is thicker than the tensioning member thickness. Tension on the cell encapsulating pouch 502 provided by the tensioning member 504 impedes collapsing or ballooning of the reservoir space 520 and thus maintains the thickness defined by the cell displacing core 550.

The tensioning member 504, as shown in FIGS. 5A-B, is isolated from the reservoir space 502 by the cell displacing core 550, although it need not be isolated if the tensioning member material is compatible with the cells to be inserted. Thus, whether the tensioning member 504 is isolated from the reservoir space 502 or not is not intended to be a limiting feature of the embodiment.

The tensioning member 504 shown in FIGS. 5A-B includes opposing ends 542, 544 that are non-linear and opposing sides 546, 548 that are substantially linear, but may be another shape that provides uniform tension across a length of the cell encapsulating pouch 502 (where the length is from one opposing end to the other). According to various embodiments, the non-linear ends 542, 544 may be non-linear in the plane defined by the X-axis 516 and Y-axis 518, as shown in FIG. 5A, and/or may be non-linear in the plane defined by the X-axis 516 and the Z-axis (not shown), in an intermediate plane, or in multiple planes. According to various embodiments, the non-linear ends may include one or more curves, as shown in FIG. 5A, or may include other non-linear shapes, such as a serpentine shape or helix. Alternatively, frames with other shapes described herein may be utilized as the tensioning member 504. As such, the precise shape of the tensioning member 504 should not be considered limiting.

The non-linear shape of the ends 542, 544 allows deformation of the tensioning member 504 from an undeformed to a deformed configuration when opposing inward forces are applied to the sides 546, 548. The tensioning member 504 is in a deformed configuration when inside the cell encapsulating pouch 502. The tendency of the tensioning member 504 to return to its undeformed configuration exerts opposing lateral forces on the cell encapsulating pouch 502 and imparts tension to the top and bottom layers 506, 508.

Figure 6A:
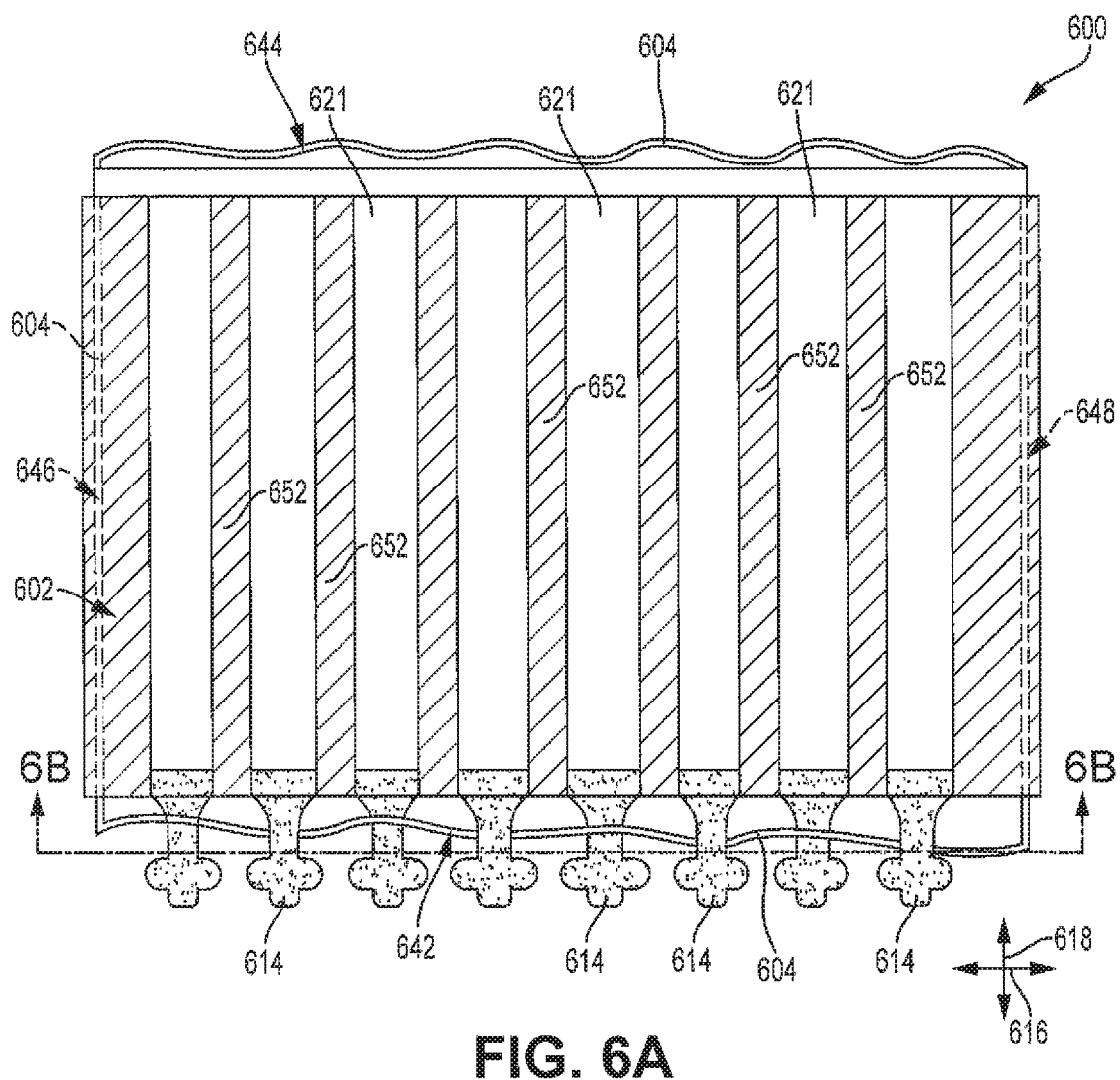
FIG. 6A is a schematic of a top view of a cell encapsulation device according to embodiments described herein.
Figure 6B:
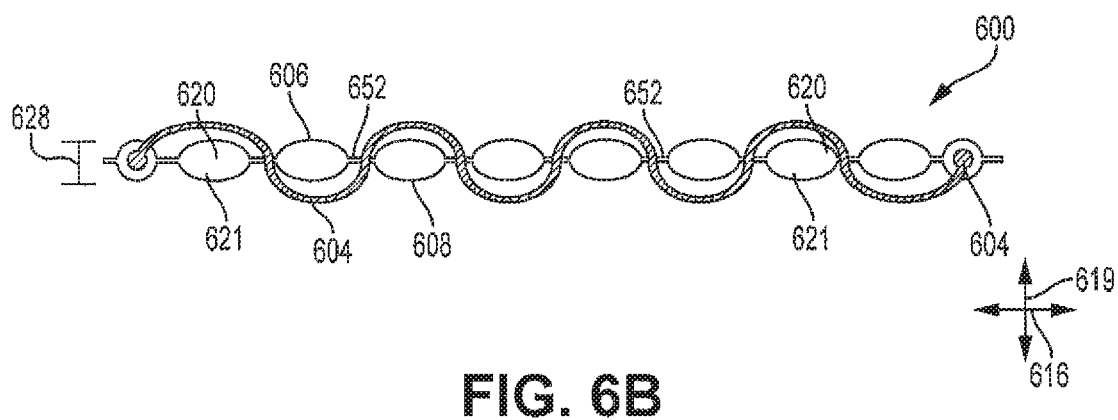
FIG. 6B is a schematic of a cross-section of the cell encapsulation device of FIG. 6A taken along line 6B-6B in FIG. 6A.

FIGS. 6A-B illustrate another embodiment of a cell encapsulation device 600 having tensioning member 604 and a cell encapsulating pouch 602. FIG. 6A is a top view of the cell encapsulation device 600, where the device is in the in the plane defined by the X-axis 616 and the Y-axis 618. FIG. 6B is a cross-sectional view of the cell encapsulation device 600 across line 6B-6B, the cross-section showing the plane defined by the X-axis 616 and Z-axis 619. The cell encapsulation device 600 has a first layer 606 and second layer 608 that are sealed together at intermediate positions 652 such that the reservoir space between the first and second layers 606, 608 is sub-divided into a plurality containment tubes 621, each containment tube 621 having a separate reservoir space therein for the containment of cells. In various examples, each containment tube 621 has a separate port 614 such that the reservoir space of each containment tube 621 may be independently loaded with cells. In some embodiments, a filling tube (not illustrated) may be inserted into the containment tubes 621. The filling tube may be pre-filled with cells. In addition, the filling tube may be extracted from the containment tube and refilled (and/or reused) as needed.

As illustrated in FIGS. 6A-B, the tensioning member 604 extends around a periphery of the cell encapsulation device 600. In the embodiment shown in FIGS. 6A-B, the tensioning member 604 is isolated from the reservoir space (i.e., not in fluid communication), and, as a result, the tensioning member may therefore be made of any suitable material, regardless of whether or not it is compatible with the encapsulated cells. The tensioning member 604 includes opposing ends 642, 644 that are non-linear and opposing sides 646, 648 that are linear. In certain embodiments, at least a portion of the tensioning member 604 is positioned between the first layer 606 and the second layer 608 (e.g., in the opposing, linear ends 646, 648 in FIGS. 6A-B) and another portion is external to the cell encapsulating pouch 602 (e.g., in the non-linear ends 642, 644 in FIGS. 6A-B). According to various embodiments, the non-linear ends 642, 644 may be non-linear in the plane defined by the X-axis 616 and Z-axis 619, as shown in FIG. 6B, and/or may be non-linear in the plane defined by the X-axis 616 and the Y-axis 618, in an intermediate plane, or in multiple planes. In the example illustrated in FIG. 6B, the non-linear ends 642, 644 are non-linear in the Z-dimension 619.

The non-linear shape of the ends 642, 644 allows deformation of the tensioning member 604 from an undeformed configuration to a deformed configuration when opposing inward forces are applied to the sides 646, 648. The tensioning member 604 is in a deformed configuration when inside the cell encapsulating pouch 602. The tendency of the tensioning member 604 to return to its undeformed configuration exerts opposing lateral forces on the cell encapsulating pouch 602 and imparts tension to the top and bottom layers 606, 608 and stretches the containment tubes 621 such that the thickness 628 of each containment tube 621 (and therefore the reservoir space) is controlled.

In some embodiments, the cell encapsulation devices described herein may include multiple tensioning members. The tensioning member(s) may be a single tensioning member that does not fully surround a reservoir space or it may be multiple tensioning members, none of which fully surround the reservoir space. The tensioning members collectively may or may not surround the reservoir space.

FIGS. 7A-D illustrate an embodiment of an insert 710 for a cell encapsulation device 700 that includes tensioning members 704a, 704b. FIG. 7A is a top view of insert 710 including a cell displacing core 750 coupled to two tensioning members 704a, 704b. The ends 705a, 705b of the tensioning members 704a, 704b are embedded in the cell displacing core 750. FIG. 7B is an end view of the insert shown in FIG. 7A. FIG. 7C is a side view of the insert shown in FIG. 7A. FIG. 7D is a cross-sectional view of the insert shown in FIG. 7A taken across line 7D-7D. FIG. 7E is a cross-sectional view across line 7D-7D of the cell encapsulation device 700 formed when the insert 710 is placed inside a cell encapsulating pouch 702. The cell encapsulating pouch 702 includes a first porous layer 706 and a second porous layer 708 that define an interior volume 712 with the tensioning members 704a, 704b and the cell displacing core 750 disposed therein. The tensioning members 704a, 704b contact two opposing portions of the cell encapsulating pouch 702, and exerts tension on the first and second layers 706, 708. The cell encapsulation device 700 includes a reservoir space 720 for receiving cells between the first porous layer 706 and the second porous layer 708 and the cell displacing core 750. In other embodiments not depicted herein, the cell encapsulating pouch 702 can be a single tubular membrane that is flattened to form the first layer 706 and the second layer 708, a single membrane folded to form the first layer 706 and the second layer 708, or two separate membranes that are layered and sealed along at least a portion of their peripheries to form the first layer 706 and the second layer 708. Alternatively, the cell encapsulating pouch could be formed from one or more membrane composites.

In some embodiments of the cell encapsulation devices described herein, the first and second layers of the cell encapsulating pouch are flexible, but the tensioning member(s) either alone or in combination with other structural components maintains the cell encapsulation device as a generally planar structure. The tensioning member or members maintain an average distance between the first and second layers under an applied force. The phrase "average distance", as used herein, is meant to describe the distance between the first interior surface and the second interior surface over a length and/or width in the reservoir of the cell encapsulation device where the cells reside and which is substantially consistent in thickness across that dimension. Advantageously, maintaining the average distance keeps the structural shape intact and avoids deformation that may result in rupture of the device. In addition, failure to maintain the average distance may result in undesirable volume changes. Optimal spacing will vary for different cell types. If the optimal average distance between the interior surfaces is exceeded, some cells within the encapsulation device will inadvertently reside too far from the device wall to receive nutrients and other biomolecules. Cells that do not receive adequate nutrients and oxygen may not be healthy and productive or may die. In some embodiments, the applied force is an external compressive force, while in other embodiments, the applied force may be an internal expansive force. In some embodiments, the applied force may be a shear force or a cyclical force. Thus, the tensioning member(s), optionally with the structural spacers may withstand both forces to maintain the average distance.

In some embodiments, the applied force may be an external compressive force that would tend to cause the reservoir space between the first and second layers to collapse in the absence of the tensioning member. For example, the surrounding tissue may exert a compressive force on the device in vivo, or a clinician may exert a compressive force on the outside of the device prior to or during insertion. If the external compressive force decreases the distance between the first and second interior surfaces, cells within the encapsulation device may be subjected to undesirable mechanical stimuli resulting in minimized cell functionality or cell fatality. In some examples, the devices are intended for subcutaneous implantation, and thus the compressive force may be caused by contact with a patient, such as a hug, a pat on the back, or a fall, while the device is implanted in the patient.

Alternatively, the applied force may be an internal expansive force that would tend to cause the reservoir space between the first and second layers to expand to a rounded, balloon-like structure in the absence of the tensioning member(s). For example, pressure may be required to inject cells into the reservoir space. In one example, pressure can be caused by over-inflation at the time of insertion, e.g., due to operator error. In another example, pressure can be caused by an increase of cells due to cellular propagation and multiplication.

In some embodiments, the tensioning member is an elastically deformable material. For example, the tensioning member may be an elastically deformable polymer, polymer blend, or metal alloy. For example, the elastically deformable material may be a polymeric elastomer, such as but not limited to natural or synthetic polyisoprene, polybutadiene, styrene-butadiene rubber, nitrile rubber, ethylene propylene rubber, ethylene propylene diene rubber, or ethylene vinyl acetate. In some embodiments, the devices described herein only require a slight amount of deflection of the tensioning member and thus a high degree of elastic and super-elastic behavior are not required. Accordingly, in some embodiments, the tensioning member may be a spring-tempered stainless steel, such as spring tempered 316 SST; a spring-tempered cobalt-chromium alloy, such as Co-28Cr-6Mo or Co-35Ni-20Cr-10Mo; or a spring-tempered titanium based alloy, such as Ti-6Al-4V. In other embodiments, the tensioning member may be a material with a high degree of elasticity. Accordingly, in some embodiments, the tensioning member may be a spring-tempered nickel-titanium alloy, such as Nitinol. The tensioning member may pre-formed into a desired shape to conform to a patient's anatomy. In addition, the tensioning member may be delivered to the desired site via a catheter or trocar.

In some embodiments, the tensioning member may be formed of or include a shape memory material. Nitinol, mentioned above, is a shape memory alloy. Other non-limiting examples of useful shape memory alloys include, but are not limited to, copper-aluminum-nickel, copper-zinc-aluminum, and iron-manganese-silicon alloys.

Other non-limiting examples of shape memory materials include shape memory polymers, such as polyetheretherketone (PEEK), polymethyl methacrylate, polyethyl methacrylate, polyacrylate, poly-alpha-hydroxy acids, polycaprolactones, polydioxanones, polyesters, polyglycolic acid, polyglycols, polylactides, polyorthoesters, polyphosphates, polyoxaesters, polyphosphoesters, polyphosphonates, polysaccharides, polytyrosine carbonates, polyurethanes, polyurethanes with ionic or mesogenic components made by a pre-polymer method, and copolymers or polymer blends thereof. Some block copolymers also show the shape-memory effect, such as, for example, a block copolymer of polyethylene terephthalate (PET) and polyethyleneoxide (PEO), block copolymers containing polystyrene and poly (1,4-butadiene), and an ABA triblock copolymer made from poly(2-methyl-2-oxazoline) and polytetrahydrofuran.

In general, a tensioning member described herein should be operable to impart tension to a cell encapsulating pouch for the life of the implanted cell encapsulation device. Accordingly, in some embodiments, a shape memory polymer useful as a tensioning members is not biodegradable. In other embodiments, however, a shape memory polymer having at least some degree of biodegradability (e.g., polyglycolic acid and some polyurethanes in the presence of certain enzymes) may be useful as a tensioning member if it can impart tension to the cell encapsulating pouch over a desired period of time.

In embodiments where the tensioning member must be biocompatible with the encapsulated cells, the tensioning member may be or may be formed of a material that is inherently biocompatible or may be a material that lacks inherent biocompatibility but is rendered biocompatible, such as with a biocompatible coating. Non-limiting examples of inherently biocompatible tensioning member materials include Nitinol and Ti-6Al-4V. Non-limiting examples of materials that could be used as a biocompatible coating include polytetrafluoroethylene (PTFE), fluorinated ethylene propylene (FEP), and parylene. Fluoropolymers that can be solvent coated may also be useful as biocompatible coatings.

In any embodiment described herein, the first and second layers of the cell encapsulating pouch optionally may be composite layers. One example of a composite layer is depicted in FIG. 2, but any embodiment described herein may optionally include a composite layer. In various examples a composite layer includes at least two layers and may include more than two layers. For example, a composite layer may include at least an outer porous layer and an inner porous layer disposed adjacent to the outer porous layer. In some embodiments, both the first and second layers of a cell encapsulating pouch may be composite materials, each having an outer porous layer and an inner porous layer. The outer porous layers of the first and second layers may be the same material or may be different materials. Likewise, the inner porous layers of the first and second layers may be the same material or may be different materials. In certain embodiments, a pore size of the inner porous layer is less than a pore size of the outer porous layer. In certain embodiments, a porosity of the inner porous layer is less than a porosity of the outer porous layer. In various embodiments, portions of the inner porous layers form the first interior surface and the second interior surface of the cell encapsulation device.

When both the first and second layers of a cell encapsulating pouch are composite layers, in some embodiments, both inner porous layers have an average pore size sufficiently small to prevent vascular ingrowth. Herein, layers that restrict or prevent vascular ingrowth may be referred to as "tight" layers. As one non-limiting example, the average pore size of the inner porous layers may be less than about 5 microns, less than about 1 micron, less than about 0.8 microns, less than about 0.5 microns, less than about 0.3 microns, or less than about 0.1 micron, as measured by porometry. In some further examples, the average pore size of the inner porous layers may range between about 0.05 and about 0.4 microns, as measured by porometry. The small pore size allows the inner porous layers to function as a cell retentive layer to keep cells disposed in the reservoir space inside the encapsulation device yet allows nutrients and other biomolecules to enter and cell waste and therapeutic products to exit. This layer is therefore sometimes referred to herein as a cell retentive layer. In some embodiments, the pores resist cellular ingrowth but are selectively permeable to certain macromolecules.

When both the first and second layers of a cell encapsulating pouch are composite layers, in some embodiments, both outer porous layers have an average pore size great enough to permit growth of vascular tissue from a patient within the pores of the outer porous layer. Herein, layers that have openings large enough to allow vascular ingrowth may be referred to as "open" layers or "vascularizing" layers. In some non-limiting examples, the pore size of the outer porous layers is greater than about 5.0 microns, greater than about 6.0 microns, greater than about 7.0 microns, or greater than about 10 microns as measured by porometry. Ingrowth of vascular tissues through the outer porous layers facilitates nutrient and biomolecule transfer from the body to the cells encapsulated in the device.

Various cell types can grow into the vascularizing layer of a porous material of cell encapsulation device as described herein. The predominant cell type that grows into a particular porous material depends primarily on the implantation site, the composition and permeability of the material, and any biological factors, such as cytokines and/or cell adhesion molecules, for example, that may be incorporated in the material or introduced through porous material(s). In some embodiments, vascular endothelium is the predominant cell type that grows into a porous material for use in a cell encapsulation device. Vascularization of the porous material by a well-established population of vascular endothelial cells in the form of a capillary network is encouraged to occur as a result of neovascularization of the material from tissues of a patient into and across the thickness of the material very close to the interior surface of the cell encapsulation device, but not across the cell retentive layer.

In some embodiments, only one of the first and second layers is a composite layer. For example, the first layer may be a composite layer including an outer porous layer that is a vascularizing layer and an inner porous layer that is a cell retentive layer, while the second layer may only include a cell retentive layer.

In another embodiment neither the first nor the second layer is a composite layer, and both are cell retentive layers. Thus, the device includes no vascularizing layer. In such embodiments, the cell encapsulation device optionally could be used with a housing that is, or can be, disposed in a patient, and that is made from a vascularizing material, such that the housing allows ingrowth of vascular tissue from a patient. In some embodiments, the housing may be implanted into a patient for a period of time sufficient to allow vascularization before the device is inserted into the housing. In other embodiments, the device and the housing may be inserted into a patient together.

In a further embodiment, neither the first nor the second layer is a composite layer, and instead, both are vascularizing layers. Thus, the device includes no cell retentive layer. In such an embodiment, the cells to be inserted into the cell encapsulation device may be microencapsulated, which provides isolation for the cells from host immune response. In some embodiments, the cells may be microencapsulated within a biomaterial of natural or synthetic origin, including, but not limited to, a hydrogel or algenate biomaterial. As a result, a separate cell retentive layer may be omitted from the cell encapsulation device.

Materials useful as outer porous vascularizing layers and inner porous cell retentive layers include but are not limited to, alginate; cellulose acetate; polyalkylene glycols such as polyethylene glycol and polypropylene glycol; panvinyl polymers such as polyvinyl alcohol; chitosan; polyacrylates such as polyhydroxyethylmethacrylate; agarose; hydrolyzed polyacrylonitrile; polyacrylonitrile copolymers; polyvinyl acrylates such as polyethylene-co-acrylic acid; porous tetrafluoroethylene (TFE) polymers such as porous polytetrafluoroethylene (PTFE) (for example, expanded PTFE (ePTFE)), porous modified PTFE, and porous TFE copolymers; porous polyalkylenes such as porous polypropylene, porous polyethylene; porous polyvinylidene fluoride; porous polyester sulfone (PES); porous polyurethanes; porous polyesters; porous PPX (ePPX); porous ultra-high molecular weight polyethylene (eUHMWPE); porous ethylene tetrafluoroethylene (eETFE); porous polylactic acid (ePLLA); and copolymers and combinations thereof, as well as woven or non-woven collections of fibers or yarns, or fibrous matrices, either alone or in combination. In some embodiments, the materials useful as porous layers include biomaterial textiles, including wovens and non-wovens.

In some embodiments, a porous vascularizing layer may be a bio-absorbable material. Alternatively, a porous vascularizing polymeric material may be coated with a bio-absorbable material or a bio-absorbable material may be incorporated into or onto a porous vascularizing polymeric material in the form of a powder. Coated materials may promote infection site reduction, vascularization, and favorable type 1 collagen deposition. The porous polymeric materials described herein may include any bio-absorbable material known in the art. Non-limiting examples of bio-absorbable materials include, but are not limited to, polyglycolide:trimethylene carbonate (PGA:TMC), polyalphahydroxy acid such as polylactic acid, polyglycolic acid, poly(glycolide), and poly(lactide-co-caprolactone), poly(caprolactone), poly(carbonates), poly(dioxanone), poly (hydroxybutyrates), poly(hydroxyvalerates), poly (hydroxybutyrates-co-valerates), and copolymers and blends thereof.

In some embodiments, structural spacers are formed from a porous material that has a pore size that excludes ingrowth of cells within the material of the structural spacers. In some embodiments the porous materials include porous PTFE (e.g., ePTFE), porous polypropylene, porous polyethylene, polyester sulfone (PES), polyurethanes, polyesters, and polyvinylidene fluoride (PVDF), either alone or in any combination.

In an alternative embodiment, the structural spacers are formed from a non-porous material. In some embodiments, the non-porous material comprises polytetrafluoroethylene (PTFE); polyurethane; polypropylene; polyethylene; polyether amide; polyetheretherketone; polyphenylsulfone; polyslfone; silicone polycarbonate urethane; polyether urethane; polycarbonate urethane; silicone polyether urethane; polyester; polyester terephthalate; melt-processable fluoropolymers, such as, for example, fluorinated ethylene propylene (FEP), tetrafluoroethylene-(perfluoroalkyl) vinyl ether (PFA), an ethylene/TFE alternating copolymer (ETFE), a tetrafluoroethylene (TFE)/hexafluoropropylene (HFP)/vinylidene fluoride (VDF) terpolymer (THV), polyvinylidene fluoride (PVDF), and combinations thereof.

In some embodiments, the structural spacers of a cell encapsulation device as described herein are adhered to the interior surfaces of one or both of the first and second layers. In some embodiments, the structural spacers are adhered to at least one inner surface, although they need not be. For example, in other embodiments, the structural spacers may be free floating within the reservoir space. In some embodiments, the first and second layers are both composite materials having inner tight porous layers, and the structural spacers are adhered to both of the inner tight porous layers.

The structural spacers may penetrate a portion of the pores of the inner tight porous layers. In some embodiments, the spacers do not penetrate the outer vascularizing porous layer so that the outer vascularizing porous layer remains undisturbed to allow for cellular ingrowth.

In some embodiments, the structural spacers may be formed by depositing a fluoropolymer powder onto a cell retentive layer to form at least a part of a structural spacer. Useful methods of powder coating are taught in U.S. Pat. No. 8,808,848 to Bacino, which is incorporated herein in its entirety.

Any material which acts to displace cells from the center of the device is suitable for use as the material of the cell displacing core. For example, suitable core materials include, but are not limited to, polytetrafluoroethylene (PTFE), expanded polytetrafluoroethylene (ePTFE), polydimethysiloxane, polyurethane, polyester, polyamide, or hydrogels derived from polysaccharides, alginate, hydrolyzed polyacrylonitrile, and combinations thereof. In some embodiments, the core is a flexible polymer or elastomer. In other embodiments, the core may be manufactured from polysaccharides, hydrophilic copolymers of polyacrylonitrile, a copolymer of polyacrylonitrile and acrylamide, and/or other non-porous polymers.

Methods for sealing the top and bottom layers include thermal welding, staking, ultrasonic sealing, and impulse heat sealing. One example of a device useful for sealing the top and bottom layers, for example, for creating the sealed periphery is an impulse heat seal. In certain embodiments, an impulse heat seal base fixture includes a silicone die plate and a matching impulse heat band geometry. A membrane or membrane composite to be sealed may be placed between the base fixture and a compressive top fixture having a mirror image silicone die plate, and the impulse heat band is compressed and heated between the silicone die plates to seal the membrane or membrane composite and form the cell encapsulating pouch.

In some examples the distance between the first and second interior surfaces, which is also the thickness of the reservoir space, is at least about 50 microns (0.05 mm) (for example, at least 0.1 mm, at least 0.15 mm, at least 0.2 mm, or at least 0.5 mm). In some examples the distance between the first and second interior surfaces, which is also the thickness of the reservoir space, is between 0.05 mm and 0.25 mm (for example, between 0.05 mm and 0.15 mm, between 0.05 mm and 0.10 mm, between 0.10 mm and 0.20 mm, between 0.10 mm and 0.15 mm, between 0.15 mm and 0.25 mm, between 0.15 mm and 0.20 mm, or between 0.20 mm and 0.25 mm). In some embodiments, a cell encapsulation device does not include a cell displacing core and has a distance between the first and second interior surfaces of between 0.05 mm and 0.25 mm. In some embodiments, a cell encapsulation device includes a cell displacing core and has a distance between the first and second interior surfaces of between 0.5 mm and 4.0 mm inclusive of the cell displacing core (for example, between 1.0 mm and 3.0 mm, between 1.0 mm and 2.0 mm, between 2.0 mm and 4.0 mm, between 2.0 mm and 3.0 mm, between 3.0 mm and 4.0 mm). In some embodiments, the thickness of the reservoir space (from a surface of a cell displacing core or other structural element to the pouch is from about 0.05 to about 0.25 mm. In one embodiment maintaining the average distance may place the first layer in a substantially parallel relationship with the second layer. It is important that the materials used in the composite layer, for example ePTFE, have sufficient tensile strength to maintain the integrity of the cell encapsulation device both during implant and in vivo.

In certain embodiments, the cell encapsulation device has an overall thickness (distance between opposing external surfaces of the cell encapsulating pouch) of less than about 5 mm, such as less than about 4 mm, such as less than about 3 mm, such as less than about 2 mm, such as less than about 1 mm. In some embodiments, the overall thickness of the cell encapsulation device is from about 0.3 mm to about 4 mm, for example, about 0.3 mm to about 1.0 mm, about 0.3 to about 0.5 mm, or about 0.5 mm to about 1.0 mm, about 1 mm to about 4 mm, about 1 mm to about 3 mm, or about 2 mm to about 4 mm. In some embodiments, a device that includes a cell displacing core can have an overall thickness of about 1 mm to about 4 mm. In some embodiments, a device without a cell displacing core can have an overall thickness of about 0.3 mm to about 0.5 mm.

In one non-limiting example, the distance between opposing sides of a tensioning member in an undeformed configuration may be about from about 5 mm to about 50 mm (e.g., about 20 mm) and the distance between opposing sides of the same tensioning member when the tensioning member is disposed in a cell encapsulating pouch in a deformed configuration may be about from about 5 mm to about 50 mm (e.g., about 15 mm).

The cell encapsulation devices described herein are useful for holding cells or other biological moieties in place in a tissue bed in a patient to allow the cells or other biological moiety to provide biological therapy to a patient. In some embodiments, the cells are introduced in the form of a suspension or slurry in a medium. The cells may be individual cells, cell aggregates, or cell clusters. As one example, the medium may be a cell culture or cell growth medium, optionally including desired nutrients. In some embodiments, insertion of the cells through the port may be accomplished using a syringe. In some embodiments, inserting the cells will apply pressure to the device, but the device will retain its general cross-sectional shape due to the tensioning member.

In some embodiments, the cells or other biological moieties are introduced to the reservoir space when the tensioning member of the cell encapsulation device is in a first deformed configuration that provides tension across the cell encapsulating pouch of the cell encapsulation device. In various embodiments, the cells or other biological moieties are introduced to the reservoir when the tensioning member is in a second deformed second deformed configuration that is more deformed (for example, narrower) than the first deformed configuration such that the tension on the cell encapsulating pouch is lessened. In some embodiments, the cells or other biological moieties are introduced to the reservoir space of the device through one or more ports while the tensioning member is in the second deformed configuration. In some embodiments, the port extends through the sealed periphery between a first and second layer of a sealed cell encapsulating pouch, so that the cells are introduced into the reservoir of the pouch through an edge of the pouch. In various embodiments, after the cells are inserted into the reservoir space, the tensioning member is released from the second deformed configuration such that the tensioning member returns to the first deformed configuration.

An encapsulation device as described herein may be implanted into a patient prior to or after insertion of cells. For example, the device may be inserted into a patient and allowed to vascularize such that vascular tissue grows into a vascularizing layer of the device. Then cells may be added while the device is in vivo. Alternatively, cells may be added to the device prior to insertion of the device into a tissue bed of a patient. For example, in some embodiments, the cell encapsulation device with cells may be provided with the tensioning member in a first deformed configuration that provides tension across the cell encapsulating pouch. The tensioning member may be deformed from a first deformed configuration to second deformed configuration that is more deformed (for example, narrower) than the first deformed configuration such that the tension on the cell encapsulating pouch is lessened. The cell encapsulation device may be inserted into a tissue bed of the patient, and the tensioning member may then be released from the second deformed configuration such that the tensioning member returns to the first deformed configuration.

In some embodiments, a material used for a tensioning member as described herein is inherently radio-opaque. Those device materials that are not inherently radio-opaque can be modified to be radio-opaque by impregnation of the material with barium, for example. Other useful methods for rendering a material radio-opaque are known to those skilled in the art. The radio-opacity of materials used to construct a device as described herein is mainly used to facilitate surgical placement of the cell encapsulation device or to locate the cell encapsulation device in a patient following implantation.

Examples

Example 1: A cell containing pouch was formed from 2 layers of a multilayered membrane by welding the 2 layers together using a flourothermoplastic film. The multilayer membrane consisted of a multi-layer expanded PTFE (ePTFE) membrane produced by combining layers of different membranes bonded together with a discontinuous fluoropolymer layer of fluorinated ethylene propylene (FEP). The inner layer (tight layer) consisted of a membrane with a smaller pore size and material properties listed in Table 3, made generally in accordance with the teachings of U.S. Pat. No. 3,953,566 to Gore, which is incorporated herein in its entirety. Using the method of Gore, a liquid lubricant is mixed with a commercially available powder of PTFE, and the mixture is extruded by a ram-type extruder or other type of extruder. The material is then expanded by rapid stretching, either uniaxially, biaxially, or multiaxially after the liquid lubricant is removed from it. The outer layer (open layer) consisted of a larger pore size membrane made generally in accordance with the teachings of U.S. Pat. No. 5,814,405 to Branca, et al., which is incorporated herein in its entirety, where a discontinuous layer of FEP was incorporated on the surface of this membrane based on the process teachings of International Patent Application Publication WO 94/13469 to Bacino, which is incorporated herein in its entirety, while allowing this substrate to still be air permeable. The attributes of this open layer are listed in Table 1. The inner layer (tight layer) was then put in contact with the outer layer (open layer). The discontinuous FEP surface was located between the two PTFE layers as they were heated above the melting temperature of the FEP to create a bonded multilayer membrane with the final properties identified in Table 1. The ePTFE multilayer membrane was hydrophilically treated.

TABLE 1

| Layer | Mass/area (g/m$^2$) | Non-Contact Thickness (μm) | Bubble Point Pressure (psi) [~kPA] | Airflow (L/hr@ 12 mbar) | MD Force to Break (lbf/in) [~N/M] | TD Force to Break (lbf/in) [~N/M] |
|---|---|---|---|---|---|---|
| First Layer Membrane | 13.20 | 34.1 | 51.80 [357.1] | 12.5 | 7.02 [1229] | 11.58 [2028] |
| Second layer membrane with discontinuous FEP | 5 (1.3 from FEP) | 34.1 | 1.70 [11.7] | | 3.87 [678] | 0.48 [84.1] |
| Final Multilayer Membrane | 17.90 | 73.4 | 52.10 [359.2] | 13.3 | 8.07 [1413] | 11.45 [2005] |

The cell containing pouch was welded on 3 sides leaving the fourth side open for cell loading access. The weld film was 125 um THV500 (available from Dyneon). The weld film was open in the center where the cells are intended to be placed. Both layers of membrane and the weld film extended approx. 1 cm beyond the weld on the outside edges of the part. One layer of the membrane was slit in two places at the open end of the active area from the weld outwards. A silicone rubber O-ring was placed between the membrane layers outside of the weld on the three sides where the membranes were welded together and above both layers of membrane where the pouch had be left open for later filling with cells. The O-ring was constrained to be in contact with the weld on the two long sides of the pouch and fixed in place by welding the membranes together on the outside of the O-ring. This allowed the silicone O-ring to act as a tension member and keep the active area under tension. Excess membrane and weld film was trimmed off. A filling needle was inserted between the layers to facilitate loading of the device with cells. After aseptic filling the needle is intended to be removed and the encapsulation of the cells completed by welding shut the open end of the pouch and removing excess membrane. In this example the tension member is isolated from the cells contained within the pouch.

Figure 8:
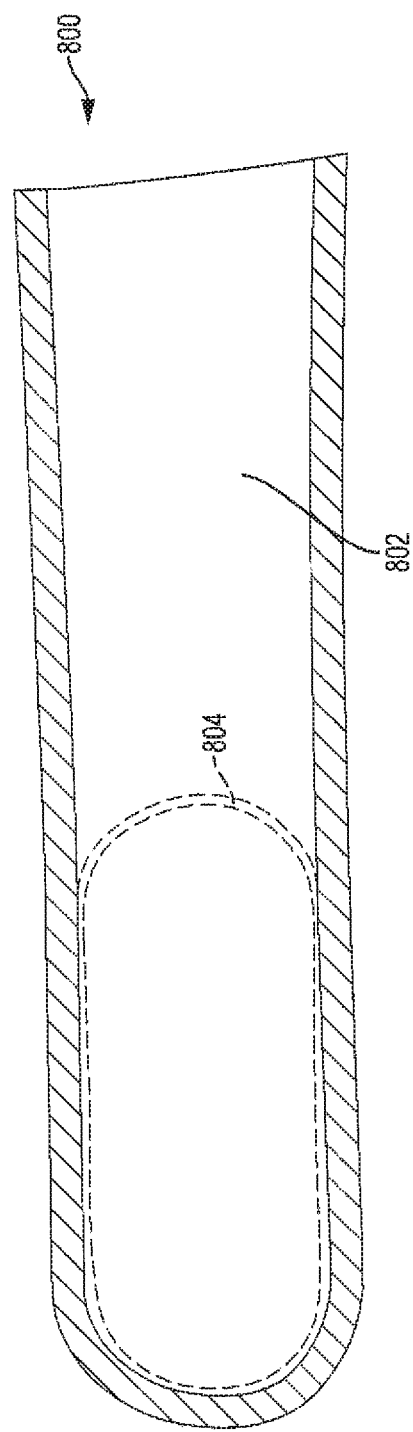
FIG. 8 is a top view of a cell encapsulation device according to embodiments described herein.

Example 2: A device containing a cell containing pouch was formed from 2 layers of a multilayer membrane by welding the 2 layers together using a flourothermoplastic film. FIG. 8 shows an exemplary device 800 with a cell encapsulating pouch 802 surrounding a tensioning member 804. Therapeutic cells can be loaded through the open end and then the end sealed/excess membrane removed to complete the combination device. In this Example, the multilayer membrane was the same composite membrane used in Example 1. The weld film was 125 um THV500 (available from Dyneon). The cell containing pouch was welded on 3 sides leaving the fourth side open for cell loading access. The weld film was open in the center where the cells are intended to be placed. Excess membrane was trimmed off of the three sides where the membranes were welded together. A tension member was formed by bending a Nitinol wire (0.27 mm) into an oval shape and thermal treating at 470° C. for 7 minutes and then quickly quenching in a water bath. The excess nitinol wire was trimmed off and the ends welded together by laser welding. The inner diameter of the pouch measured approximately 8 mm from inside of the welds. The tension member undeformed measured approximately 9 mm on the outside of the long edges. The long edges of the tension member were compressed together with a pair of tweezers to a distance of approximately 6 mm and the tension member placed into the pouch. The tension member was released and the tweezers were removed.

Example 3: A first porous expanded polytetrafluoroethylene (ePTFE) membrane was made generally in accordance with the teachings of U.S. Pat. No. 3,953,566 to Gore, which is incorporated herein in its entirety. Using the method of Gore, a liquid lubricant is mixed with a commercially available powder of PTFE, and the mixture is extruded by a ram-type extruder or other type of extruder. The material is then expanded by rapid stretching, either uniaxially, biaxially, or multiaxially after the liquid lubricant is removed from it. The membrane had a mass per unit area of about 2.43 g/m$^2$, a thickness of about 8.9 μm, a density of about 0.27 g/cc, a longitudinal matrix tensile strength of about 663 MPa, a transverse matrix tensile strength of about 14.3 MPa, and an IPA bubble point of about 4.83 kPA.

A second porous expanded polytetrafluoroethylene (ePTFE) membrane was made generally in accordance with the teachings of U.S. Pat. No. 5,476,589 to Bacino, which is incorporated herein in its entirety. The film had a mass per unit area of about 1.46 g/m$^2$, a thickness of about 0.00012 inches [~3.05 μm], a density of about 0.48 g/cc, a longitudinal matrix tensile strength of about 101,321 psi (approximately 699 MPa), a transverse matrix tensile strength of about 9288 psi (approximately 64.04 MPa), and an IPA bubble of about 35.27 psi (approximately 243.2 kPa).

A third porous expanded polytetrafluoroethylene (ePTFE) membrane was made generally in accordance with the teachings of U.S. Pat. No. 5,814,405 to Branca, which is incorporated in its entirety. The film had a mass per unit area of 6.23 grams/m$^2$, a thickness of 0.0017 inches (approximately 43.2 μm), an IPA bubble point of 0.41 psi (approximately 2.83 kPA), a longitudinal tensile strength of about 27974 psi (approximately 192.87 MPa), and a transverse matrix tensile strength of about 5792 psi (approximately 39.93 MPa).

A multi tube cell containing structure was manufactured by making a continuous length of the first ePTFE membrane into a tube with an inside diameter of approximately 13 mm generally in accordance with U.S. Pat. No. 6,617,151 to Newman, et al. (FIG. 9, steps 902 through 910 and corresponding text), which is incorporated herein in its entirety. The cell containment tubes were formed with one (1) longitudinal wrap of the first ePTFE membrane, six (6) overlapping helical wraps of the second ePTFE membrane, and one (1) overlapping wrap of the third ePTFE membrane. The tube was treated with a hydrophilic coating and removed from the core. The tube was trimmed to length and one end was sealed shut with a flourothermoplastic (THV 500) weld.

A tension member was formed from a 0.5 mm nitinol wire and bending around a jig to form a shape with 2 parallel sides and 2 sides with a "M" shape to control the deflection when the parallel sides were deformed. The formed nitinol was heated to 470° C. for 7 minutes and quickly cooled by quenching in water. The formed nitinol was removed from the jig and the end welded together with a laser welder. The parallel sides measured approximately 22 mm apart.

The tension member was deformed by moving the parallel sides together with a pair of tweezers to a distance of approximately 15 mm and the tension member placed inside of the ePTFE tube with one "M" shaped end of the tension member in contact with the welded shut end of the ePTFE tube.

The device was prepared for loading by adding a containment tube and an end seal to the open end of the tube. It was observed when the parallel edges of the tension member were compressed toward each other the center of the lumen opened up. When the external force compressing the parallel edges together was release the device returned to having a lumen thickness dimension determined by the thickness of the tension member.

Example 4: An ePTFE tube was constructed as described in Example 3. A Nitinol tension frame was formed by bending a 0.37 mm nitinol wire around a jig which formed the wire into a shape with 2 parallel edges and 2 edges with a multi wave shaped end. The Nitinol was heated to 470° C. for 7 minutes and then quickly cooled in a room temperature water bath. The formed nitinol wire was removed from the jig, excess wire removed and the ends welded together with a laser welder. The parallel edges of the tension member measured approximately 23 mm apart.

A cell displacing core was formed from a thermoplastic fluoropolymer (Gore polymerized from TFE, HFP, VDF) in a compression mold. The mold was cut from aluminum to give a negative shape of the insert with a generally oval shape. On one end of the oval a space was left to facilitate cell loading. The edge of the insert was about 0.25 mm thicker than the center to provide a controlled lumen thickness when the membrane was stretch over the thicker edge.

Figure 9:
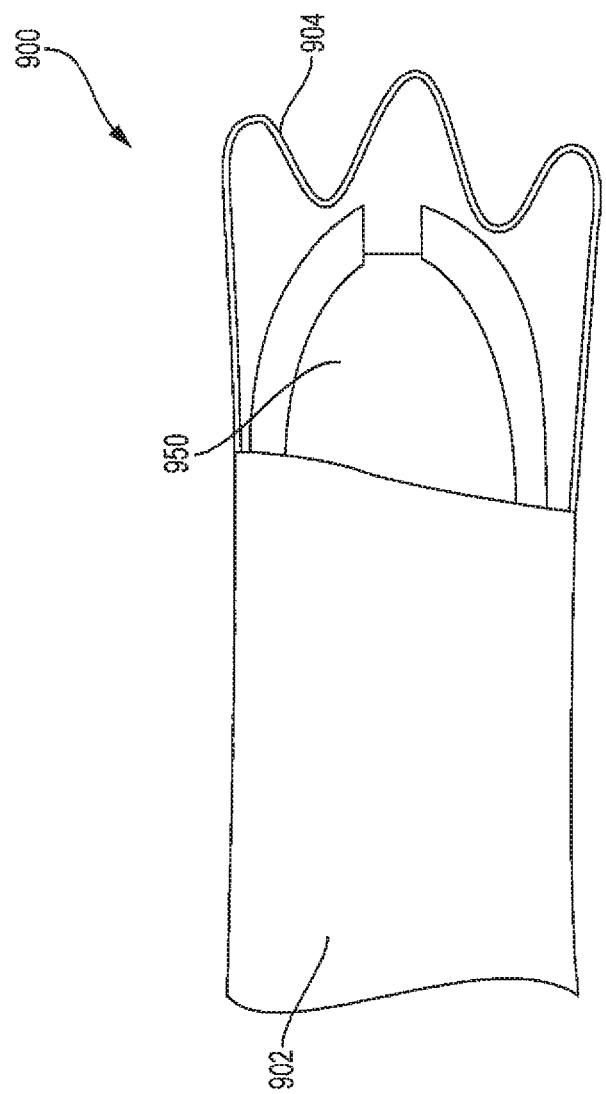
FIG. 9 is a top view of a cell encapsulation device according to embodiments described herein.

The tension member was inserted into the tube as described in example 3 and then the cell displacing core was placed into the tube. FIG. 9 shows the device 900 partially assembled. It can be appreciated that a core and tension member can be placed together into a cell encapsulating pouch 902 without impacting the intent of this patent. It can be further appreciated that a core and tension member can be preassembled or that a core can hold tension members in position that are not continuous but instead attached to the core to provide the desired force. The device could be finished as described in Example 3.

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

That which is claimed:

1. A cell encapsulation device comprising:
   a cell encapsulating pouch comprising a first layer sealed along a portion of its periphery to a second layer along a portion of its periphery to define an interior volume between the first and second layers, wherein the interior volume comprises a first interior surface and an opposing second interior surface spaced apart from the first interior surface;
   at least one tensioning member disposed within the interior volume and contacting at least two opposing portions of the cell encapsulating pouch to exert opposing forces on the cell encapsulating pouch that urge the first layer and the second layer apart from each other and thereby maintain an average distance between the first interior surface and the second interior surface; and
   a reservoir space for receiving cells within the interior volume between the first and second interior surfaces.

2. The cell encapsulation device of claim 1, wherein the first and second layers comprise top and bottom portions, respectively, of a single tube-shaped membrane or membrane composite that is at least partially flattened, and wherein the first and second layers are sealed along the portion of their peripheries at least at one end of the tube-shaped membrane or membrane composite.

3. The cell encapsulation device of claim 1, wherein the first and second layers comprise separate membranes or membrane composites.

4. The cell encapsulation device of claim 1, further comprising at least one cell displacing core within the interior volume.

5. The cell encapsulation device of claim 4, wherein the cell displacing core defines the average distance between the first interior surface and the second interior surface.

6. The cell encapsulation device of claim 1, further comprising a plurality of structural spacers within the interior volume.

7. The cell encapsulation device of claim 6, wherein the first layer is sealed to the second layer between the tensioning member and the structural spacers, and wherein the structural spacers define the average distance between the first interior surface and the second interior surface.

8. The cell encapsulation device of claim 1, wherein the at least one tensioning member is isolated from the reservoir space.

9. The cell encapsulation device of claim 1, wherein the first layer is sealed via a seal to the second layer between the tensioning member and the reservoir space to isolate the tensioning member from the reservoir space.

10. The cell encapsulation device of claim 9, wherein the seal comprises a thickness that defines the average distance between the first interior surface and the second interior surface.

11. The cell encapsulation device of claim 1, wherein the at least one tensioning member comprises a shape memory alloy or an elastomer.

12. The cell encapsulation device of claim 1, wherein the at least one tensioning member is a frame comprising opposing ends that are non-linear and opposing sides that are linear to provide uniform tension across a length of the cell encapsulating pouch.

13. The cell encapsulation device of claim 1, wherein the device comprises at least two tensioning members.

14. The cell encapsulation device of claim 1, wherein the at least one tensioning member is adjustable between a deformed configuration and an undeformed configuration such that a distance between at least two opposing sides of the at least one tensioning member is adjustable, wherein the distance between the at least two opposing sides in the deformed configuration is less than the distance between the at least two opposing sides in the undeformed configuration.

15. The cell encapsulation device of claim 1, wherein the average distance is at least a thickness of the at least one tensioning member.

16. The cell encapsulation device of claim 1, wherein the average distance is less than a thickness of the at least one tensioning member.

17. The cell encapsulation device of claim 1, wherein the cell encapsulating pouch comprises a vascularizing layer.

18. The cell encapsulation device of claim 1, wherein the cell encapsulating pouch is a membrane composite comprising an outer porous layer and an inner porous layer adjacent to the outer porous layer, and wherein a porosity of the inner porous layer is less than a porosity of the outer porous layer.

19. The cell encapsulation device of claim 1, further comprising at least one port in fluid communication with the reservoir space.

20. A cell encapsulation device comprising:
a plurality of interconnected containment tubes comprising a first end, a second end opposite the first end, and an interior reservoir space, the containment tubes being interconnected by welds, quilting, adhesive, or structural supports; and
a tensioning member disposed around at least a portion of a perimeter of the plurality of containment tubes,
wherein the tensioning member maintains an average thickness of each of the containment tubes.

21. The cell encapsulation device of claim 20, wherein the containment tubes are arranged substantially parallel to each other with the first ends aligned with each other and the second ends aligned with each other.

22. The cell encapsulation device of claim 20, wherein the tensioning member comprises at least two arcuate portions comprising alternating concavities positioned at the first end and at the second end of each of the containment tubes.

23. The cell encapsulation device of claim 20, wherein at least a portion of the tensioning member is attached to one or more containment tubes with an adhesive.

24. The cell encapsulation device of claim 20, wherein a portion of the tensioning member is retained within outermost containment tubes of the plurality of containment tubes at opposing ends of the cell encapsulation device.

25. A method of encapsulating cells comprising
providing a cell encapsulation device of claim 1, wherein the tensioning member is in a first deformed configuration that provides tension across the cell encapsulating pouch;
deforming the tensioning member from the first deformed configuration to a second deformed configuration that is more deformed than the first deformed configuration, relative to an undeformed configuration, whereby the tension on the cell encapsulating pouch is lessened;
inserting cells into the reservoir space; and
releasing the tensioning member to the first deformed configuration.

26. A method of inserting a cell encapsulation device into a patient comprising
providing a cell encapsulation device of claim 1, wherein the cell encapsulation device further comprises cells disposed in the reservoir space, and wherein the tensioning member is in a first deformed configuration that provides tension across the cell encapsulating pouch;
deforming the tensioning member from the first deformed configuration to a second deformed configuration that is more deformed than the first deformed configuration, relative to an undeformed configuration, whereby the tension on the cell encapsulating pouch is lessened;
implanting the cell encapsulation device into a tissue bed of a patient; and
releasing the tensioning member to the first deformed configuration.

27. A cell encapsulation device comprising:
a cell encapsulating pouch comprising a first layer sealed along a portion of its periphery to a second layer along a portion of its periphery to define an interior volume between the first and second layers, wherein the interior volume comprises a first interior surface and an opposing second interior surface spaced apart from the first interior surface;
a tensioning member disposed within the interior volume and contacting at least two opposing portions of the cell encapsulating pouch to exert opposing forces on the cell encapsulating pouch that urge the first layer and the second layer apart from each other and thereby maintain an average distance between the first interior surface and the second interior surface, wherein the tensioning member is a frame comprising opposing ends that are non-linear and opposing sides that are linear to provide uniform tension across a length of the cell encapsulating membrane or membrane composite; and a reservoir space for receiving cells within the interior volume between the first and second interior surfaces, wherein the reservoir space is in fluid communication with the tensioning member.

28. A cell encapsulation device comprising:

a cell encapsulating pouch comprising a first layer sealed along a portion of its periphery to a second layer along a portion of its periphery to define an interior volume between the first and second layers, wherein the interior volume comprises a first interior surface and an opposing second interior surface spaced apart from the first interior surface;

at least one tensioning member disposed within the interior volume and contacting at least two opposing portions of the cell encapsulating pouch to exert opposing forces on the cell encapsulating pouch that urge the first layer and the second layer apart from each other and thereby maintain an average distance between the first interior surface and the second interior surface; and a reservoir space for receiving cells within the interior volume between the first and second interior surfaces, wherein the first layer is sealed via a seal to the second layer between the tensioning member and the reservoir space to isolate the tensioning member from the reservoir space.

29. The cell encapsulation device of claim 28, wherein the seal comprises a thickness that defines the average distance between the first interior surface and the second interior surface.

30. The cell encapsulation device of claim 28, further comprising a plurality of structural spacers within the interior volume inward from the seal, wherein the structural spacers define the average distance between the first interior surface and the second interior surface.

31. A cell encapsulation device comprising:

a cell encapsulating pouch comprising a first layer sealed along a portion of its periphery to a second layer along a portion of its periphery to define an interior volume between the first and second layers, wherein the interior volume comprises a first interior surface and an opposing second interior surface spaced apart from the first interior surface;

at least one tensioning member disposed within the interior volume and contacting at least two opposing portions of the cell encapsulating pouch to exert opposing forces on the cell encapsulating pouch that urge the first layer and second layer apart from each other and thereby maintain an average distance between the first interior surface and the second interior surface;

a cell displacing core within the interior volume, wherein the cell displacing core defines the average distance between the first interior surface and the second interior surface; and a reservoir space for receiving cells within the interior volume between the first and second interior surfaces and adjacent to at least a portion of the cell displacing core.

32. The cell encapsulation device of claim 31, wherein the at least one tensioning member comprises two tensioning members embedded in opposite sides of the cell displacing core.

* * * * *